(12) United States Patent
Nguyen et al.

(10) Patent No.: US 11,865,362 B2
(45) Date of Patent: Jan. 9, 2024

(54) BEAM SELECTION FOR RADIOTHERAPY

(71) Applicant: The Board of Regents of The University of Texas System, Austin, TX (US)

(72) Inventors: Dan Nguyen, Dallas, TX (US); Azar Sadeghnejad Barkousaraie, Dallas, TX (US); Steve Jiang, Southlake, TX (US)

(73) Assignee: The Board of Regents of University of Texas System, Austin, TX (US)

(*) Notice: Subject to any disclaimer, the term of this patent is extended or adjusted under 35 U.S.C. 154(b) by 792 days.

(21) Appl. No.: 16/863,147

(22) Filed: Apr. 30, 2020

(65) Prior Publication Data

US 2021/0339048 A1   Nov. 4, 2021

(51) Int. Cl.
*A61N 5/10* (2006.01)
*G16H 30/20* (2018.01)
*G16H 20/40* (2018.01)

(52) U.S. Cl.
CPC .......... *A61N 5/1031* (2013.01); *A61N 5/1036* (2013.01); *A61N 5/1039* (2013.01); *A61N 5/1045* (2013.01); *G16H 20/40* (2018.01); *G16H 30/20* (2018.01); *A61N 2005/1034* (2013.01)

(58) Field of Classification Search
CPC ........ G16H 20/40; G16H 30/40; G16H 50/20; A61N 5/1031; A61N 5/1039; A61N 5/1045; G06N 3/08
See application file for complete search history.

(56) References Cited

U.S. PATENT DOCUMENTS

2013/0197878 A1*  8/2013  Fiege ...................... G06F 30/20
                                                          703/2

* cited by examiner

*Primary Examiner* — Christine H Matthews
(74) *Attorney, Agent, or Firm* — DLA Piper LLP US

(57) ABSTRACT

A method for determining a radiotherapy treatment plan can include: receiving anatomical data for a patient; generating, via a neural network analyzing the anatomical data, a plurality of fitness values for a plurality of candidate beam orientations; determining a selected beam orientation based on the plurality of fitness values; performing a fluence map optimization (FMO) process on the selected beam orientation; and determining a dose distribution for the patient based on the FMO process.

17 Claims, 16 Drawing Sheets

BEAM SELECTION FOR RADIOTHERAPY

BACKGROUND

External beam radiation therapy (EBRT) is a common treatment method for various types of cancers. EBRT can involve using a machine to emit high-energy radiation to a patient's body to damage cancerous cells. Radiation beams, however, may not distinguish between healthy and cancerous cells while traveling through the patient's body, which can cause damage to healthy tissue and critical internal structures. Excessive damage to healthy critical structures can degrade the patient's qualify of life by adding undesirable toxicity to healthy tissues and/or organs.

SUMMARY

According to one aspect of the present disclosure, a method for determining a radiotherapy treatment plan can include: receiving anatomical data for a patient; generating, via a neural network analyzing the anatomical data, a plurality of fitness values for a plurality of candidate beam orientations; determining a selected beam orientation based on the plurality of fitness values; performing a fluence map optimization (FMO) process on the selected beam orientation; and determining a dose distribution for the patient based on the FMO process. In some embodiments, the method can include configuring a multi-leaf collimator (MLC) to administer the dose distribution at the selected beam orientation.

In some embodiments, anatomical data can include: at least one image of a tumor within the patient, wherein each of the at least one image can include contours defining a plurality of organs at risk (OARs); and a plurality of structure weights associated with the plurality of OARs. In some embodiments, determining the selected beam orientation can include using an argmax function to identify a beam orientation associated with a maximum or a minimum fitness value of the plurality of fitness values. In some embodiments, determining the selected beam orientation can include using a tree-search algorithm to identify a solution from a decision space of the neural network.

In some embodiments, using a tree-search algorithm to identify the solution from the decision space of the neural network can include iteratively selecting a branch based on a probability distribution of the neural network and updating the probability distribution after each selection. In some embodiments, wherein each fitness value of the plurality of fitness values can be a prediction of a value based on dual feasibility optimality conditions. In some embodiments, the neural network can include a convolutional up-sampling stage.

According to another aspect of the present disclosure, a method for determining a radiotherapy treatment plan can include receiving anatomical data for a patient; receiving beam orientation data, wherein beam orientation data can include information on pre-selected beam orientations; generating, via a neural network analyzing the anatomical data and the beam orientation data, a first plurality of fitness values for a plurality of candidate beam orientations; determining a first selected beam orientation based on the first plurality of fitness values; generating updated beam orientation data that can include information associated with the first selected beam orientation; generating, via the neural network analyzing the anatomical data and the updated beam orientation data, a second plurality of fitness values for the plurality of candidate beam orientations; determining a second selected beam orientation based on the second plurality of fitness values; performing a fluence map optimization (FMO) process on the first and second selected beam orientations; and determining a dose distribution for the patient based on the FMO process.

In some embodiments, the method can include configuring a multi-leaf collimator (MLC) to administer the dose distribution at the first and second selected beam orientations. In some embodiments, anatomical data can include at least one image of a tumor within the patient, wherein each of the at least one image can include contours defining a plurality of organs at risk (OARs); and a plurality of structure weights associated with the plurality of OARs. In some embodiments, determining a selected beam orientation can include using an argmax function to identify a beam orientation associated with a maximum or a minimum fitness value of a plurality of fitness values.

In some embodiments, determining a selected beam orientation can include using a tree-search algorithm to identify a solution from a decision space of the neural network. In some embodiments, using a tree-search algorithm to identify the solution from the decision space of the neural network can include iteratively selecting a branch based on a probability distribution of the neural network and updating the probability distribution after each selection. In some embodiments, each fitness value of the first and second pluralities of fitness values can be a prediction of a value based on dual feasibility optimality conditions. In some embodiments, generating, via the neural network analyzing the anatomical data and the beam orientation data, the first plurality of fitness values for the plurality of candidate beam orientations can include generating a complement of the beam orientation data; and generating the first plurality of fitness values for the plurality of candidate beam orientations based on the anatomical data, the beam orientation data, and the complement of the beam orientation data. In some embodiments, the neural network can include a convolutional up-sampling stage.

According to another aspect of the present disclosure, a method for training a neural network architecture can include: generating a training dataset based on a plurality of patient images, the patient images comprising contours defining planning target volumes (PTVs) and organs at risk (OARs), wherein the dataset can include a plurality of patient sets; approximating a fluence map optimization (FMO) solution for each patient set of the plurality of patient sets; generating a plurality of fitness values for each patient set, wherein a fitness value can be based on a dual feasibility optimality condition of the FMO solution; configuring a neural network to predict fitness values based on the training dataset and beam orientation data; and using a loss function and backpropagation to train the neural network. In some embodiments, the method can include configuring the neural network to predict fitness values based on the training dataset, the beam orientation data, and a complement of the beam orientation data. In some embodiments, the neural network can include a convolutional up-sampling stage.

BRIEF DESCRIPTION OF THE DRAWINGS

Various objectives, features, and advantages of the disclosed subject matter can be more fully appreciated with reference to the following detailed description of the disclosed subject matter when considered in connection with the following drawings, in which like reference numerals identify like elements.

Figure 1:
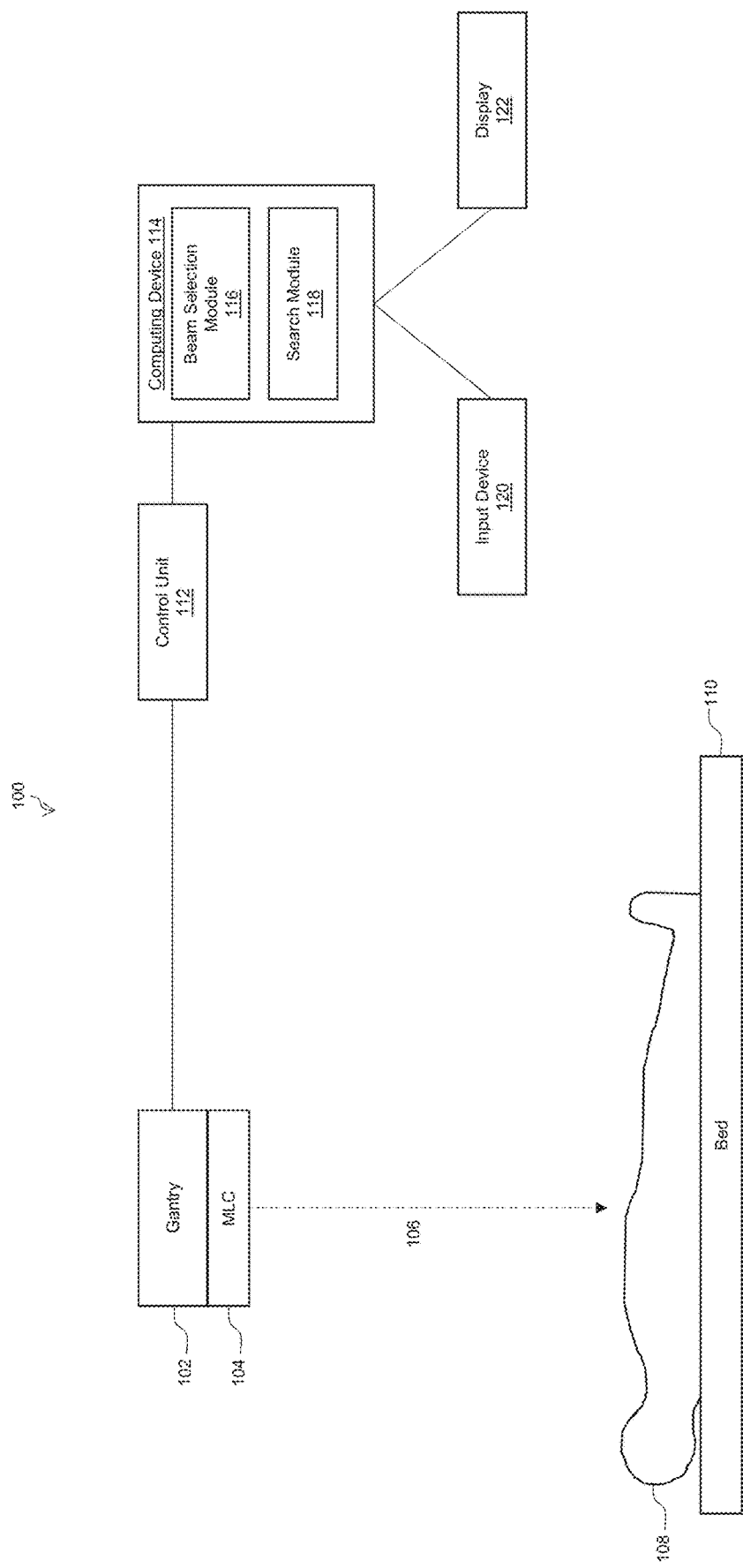
FIG. 1 is an illustrative system for intensity modulated radiation therapy (IMRT), according to some embodiments of the present disclosure.

The drawings are not necessarily to scale, or inclusive of all elements of a system, emphasis instead generally being placed upon illustrating the concepts, structures, and techniques sought to be protected herein.

DETAILED DESCRIPTION

The following detailed description is merely exemplary in nature and is not intended to limit the invention or the applications of its use.

Intensity-modulated radiation therapy (IMRT) is a method of EBRT that can deliver radiation beams (e.g. beams of photons, electrons, or heavy ions) with various intensities and from different static directions toward a planning target volume (PTV). A PTV may refer to the volume of a tumor or the desired volume to receive radiation; a PTV can also include margins around the edge of the tumor or desired volume. Additionally, a treatment plan may attempt to avoid delivering radiation to organs at risk (OAR). For IMRT, the body of the patient can be irradiated from fixed beam locations around the patient. The radiation beams can be provided by a linear accelerator (LINAC) and the radiation field can be modulated at each beam position using multi-leaf collimators (MLC). The configuration of beam directions and selection of beam orientations can affect the quality of a treatment plan and influence both the final outcome and patient's quality of life. However, current clinical protocols can either have the beam orientations selected by protocol or manually by the treatment planner, which can involve time-consuming trial-and-error processes and possibly sub-optimal choices. It is common for a physician and/or dosimetrist to visually analyze images of tumors and organs within a patient's body and determine a treatment plan to deliver radiation sufficient to kill the tumor; the treatment plan can be determined by the physician based on past experiences and information from other patients that have been treated.

Various beam orientation optimization methods (BOO) can be used to solve for a suitable set of beam angles by solving an objective function to a local minimum or maximum, such as a column generation method. To measure the impact of a BOO solution, a fluence map optimization (FMO) can also be solved. FMO can involve finding the appropriate intensities for the selected beams to generate a treatment plan. However, modern BOO methods and FMO can be computationally complex, expensive, and time intensive operations, taking hours to compute. As a result, BOO methods have not been adopted clinically. For example, column generation algorithms, when used for beam orientation optimization, can generate fitness values for a first beam and then run an FMO for the selected beam, Then, the column generation algorithm can use the "optimized" dose from the FMO to calculate fitness values to select the second beam. This alternation between the FMO and the fitness value calculation can help generate effective solutions but can also be computationally expensive and slow.

Embodiments of the present disclosure relate to systems and methods for using a deep neural network architecture to predict beam orientation fitness values for radiotherapy treatments, such as IMRT. The neural network architecture can be used to select beam orientations for a patient based on anatomical data from the patient, such as images of a tumor and organs and/or structures surrounding the tumor. In some embodiments, the neural network can learn the connection between a patient's anatomy and fitness values of an optimization algorithm for a set of beam orientations. Once a set of beams has been selected, FMO may be performed on the selected beams to generate a final treatment plan (e.g. to include intensities for each beam). In practice, the FMO can be used to configure multi-leaf collimators to generate the actual radiation field to be used for treatment. In some embodiments, the neural network can be used to predict beam orientations over time scales that are viable for clinical applications (e.g. seconds to minutes). In some embodiments, a tree-search algorithm can be combined with the neural network architecture to search the decision space of the neural network and select beam orientations. In some embodiments, the methods described herein can be applied to either coplanar or non-coplanar radiation therapy.

FIG. 1 is an illustrative system 100 for intensity modulated radiation therapy (IMRT), according to some embodiments of the present disclosure. In some embodiments, system 100 can include a gantry 102, a multi-leaf collimator (MLC) 104, a radiation beam 106, a patient 108, a bed 110, a control unit 112, and a computing device 114. In some embodiments, computing device 114 can include beam selection module 116 and search module 118, as well as input device 120 and display 122.

In some embodiments, beam selection module 116 can be configured to use a neural network architecture to predict beam orientation fitness values for radiotherapy applications. In some embodiments, computing device 114 can be configured to receive patient data (e.g. image data and structure weight data as further described herein) and feed the patient data as an input to a neural network architecture in beam selection module 116. In some embodiments, beam selection module 116 can be configured to generate a fitness value function based on patient anatomical data, determine a beam orientation based on the fitness value function, and perform FMO on a selected beam angle (e.g. see blocks 902-904 of FIG. 9). In some embodiments, search module 118 can be configured to utilize a tree search algorithm to determine beam orientations within the decision space of the neural network architecture.

In some embodiments, control unit 112 can be configured to receive instructions from computing device 114 regarding selected beam orientations. Control unit 112 can be configured to control the gantry 102, MLC 104, and bed 110 in accordance with providing a selected radiotherapy treatment plan.

In some embodiments, computing device 114 can include one or more computing devices capable of receiving user input as well as transmitting and/or receiving data over a network. In some embodiments, computing device 114 can include a conventional computer system, such as a desktop or laptop computer. Alternatively, computing device 114 may include a device having computer functionality, such as a personal digital assistant (PDA), a mobile telephone, a smartphone, or other suitable device. In some embodiments, computing device 114 may be the same as or similar to device 1500 described below in the context of FIG. 15.

Figure 2:
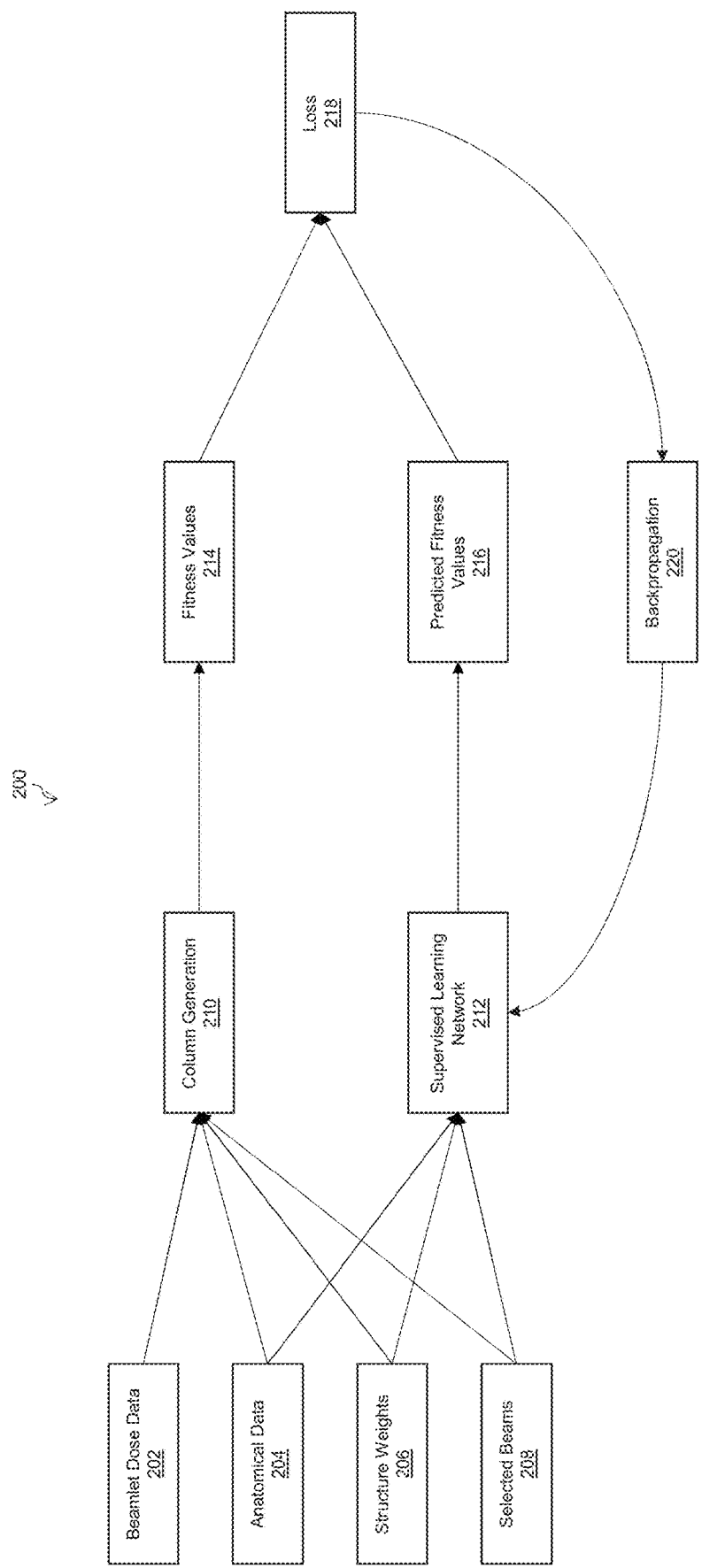
FIG. 2 is an illustrative training framework, according to some embodiments of the present disclosure.

FIG. 2 is an illustrative training framework 200, according to some embodiments of the present disclosure. In some embodiments, framework 200 can be used to train a neural network to predict fitness values for beam selection in radiotherapy applications. In some embodiments, framework 200 may utilize supervised learning to train a neural network; the supervised learning can train the network weights such that the neural network can have the minimum difference from teacher-given, real-valued labels or targets. In framework 200, a column generation algorithm (210) can be used as the teacher, and the fitness values (214) can be used as target labels. Framework 200 can include input data, such as beamlet dose data 202, anatomical data 204, structure weights 206, selected beams 208, a column generation algorithm 210, a supervised learning network 212, fitness values 214, predicted fitness values 216, a loss function 218, and backpropagation 220.

In some embodiments, beamlet dose data 202 can include the dose contribution to the volume of interest from each individual element of the fluence map (herein referred to as a beamlet). Anatomical data 204 can include images of a tumor and organs/tissue surrounding the tumor in a patient. In some embodiments, the images can include contours or contoured images, where the contours define different organs or types of tissue. Structure weights 206 can be numerical weights that reflect the importance of an organ and can be assigned to each contoured structure or organ within the anatomical data 204. For example, a higher weight may reflect a more important need for avoiding radiation being delivered to that organ. In some embodiments, selected beams 208 can include the set of currently selected beams. In the case of an iterative approach, selected beams 208 can initially be zero (e.g. no selected beams). However, selected beams 208 can include any number of beams. In some embodiments, to train the neural network, images of clinical cancer patients can be augmented by rotation and a random OAR weight generator to form input samples. For example, for patients with prostate cancer, images that include six contours can be used; contours can be of the PTV, body, bladder, rectum, left femoral head, and right femoral head. Additionally, skin and ring tuning structures can be added to control high dose spillage and conformity in the body and to train and test the network. In some embodiments, images can be divided randomly into two exclusive sets: a model development set that includes training and validation data, and a test data set.

Figure 14A:
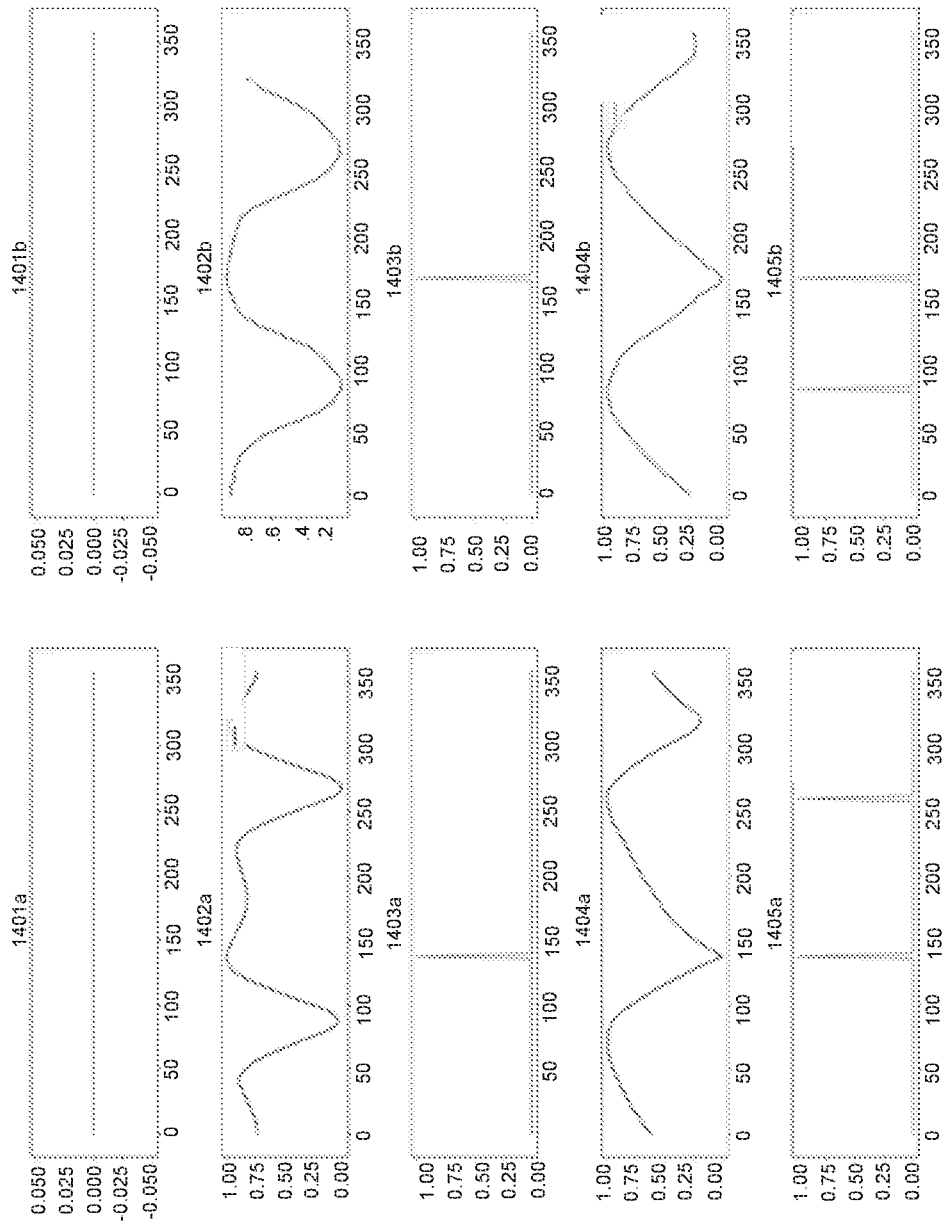
FIGS. 14A-14B show self-correction results for a neural network architecture and a column generation algorithm, according to some embodiments of the present disclosure.
Figure 14B:
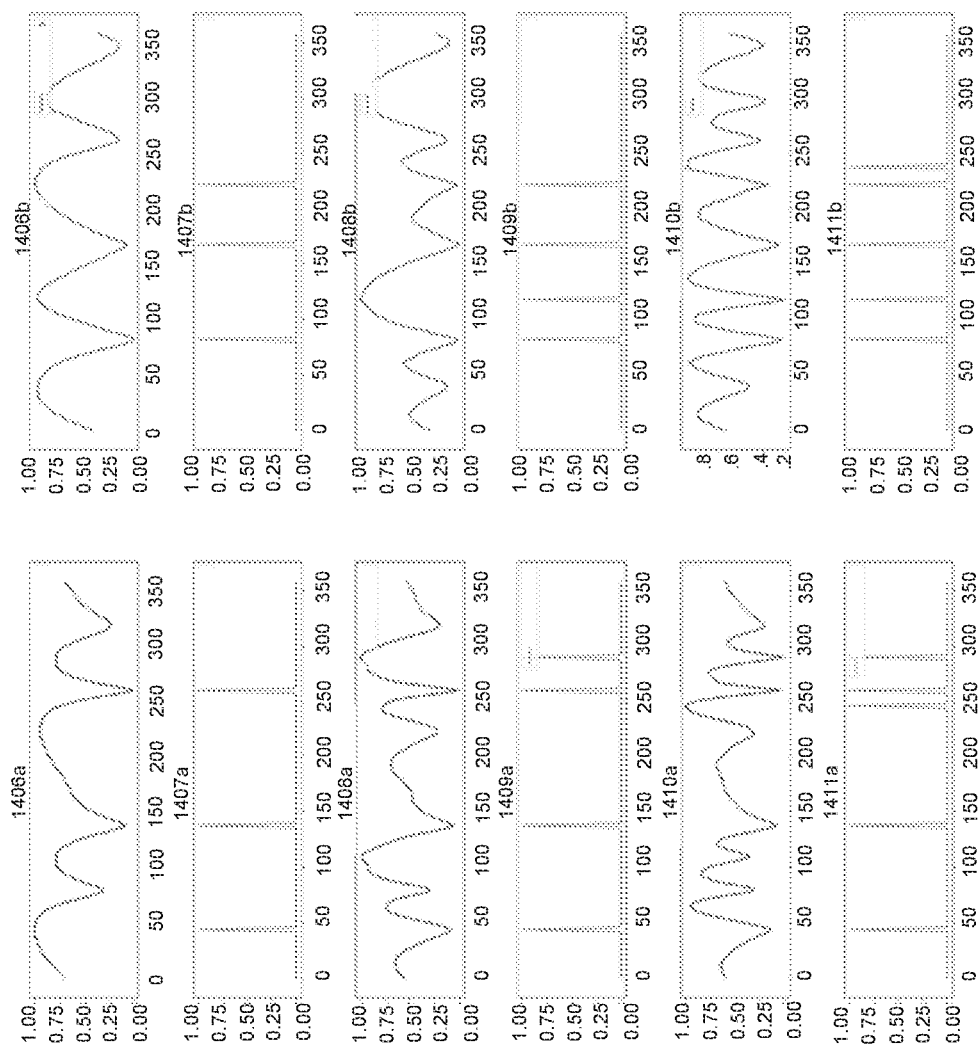

In some embodiments, training data can be created by using the column generation algorithm 210 to select sets of five beams for each set of input data. In some embodiments, training data can also include starting with a random selection of one to four beams as being part of the solution set and then using the column generation algorithm 210 to select the next beams. In some embodiments, this can allow the network 212 to learn how the column generation algorithm 210 compensates for when a suboptimal beam set is introduced as an input. In some embodiments, by learning how to "compensate" for when a suboptimal beam is selected, the network 212 can learn how to self-correct in the case that it makes a poor beam selection. Examples of self-correction results are shown in FIGS. 14A-B. In some embodiments, the structure weights 206 can be selected by various processes to be included as training data. In some embodiments, a uniform distribution in the range of 0 to 0.1 can be used to generate a weight for each OAR separately. In some embodiments, a uniform distribution in the range of 0 to 0.05 can be used to select weights for OARs separately. In some embodiments, specific values can be preselected for each OAR, such as [0, 0.2] for the bladder, [0, 0.2] for the rectum, [0, 0.1] for the right femoral head, [0, 0.1] for the left femoral head, [0, 0.1] for the shell, and [0, 0.3] for the skin. In some embodiments, these weighting schemes can provide clinically reasonable doses for training data. Each structure weights 206 generation technique can be used on each set of patient data to generate additional training data sets (e.g. and can be used in multiple instances to generate additional sets). In some embodiments, the sets of patient data can also be rotated ninety degrees to allow for additional training data sets.

The column generation algorithm 210 can receive beamlet dose data 202, anatomical data 204, structure weights 206, and selected beams 208 as input data and calculate fitness values 214 for selected beam orientations. Note, framework 200 can be applicable or compatible with any iterative optimization algorithm and column generation 210 is merely exemplary in nature. In some embodiments, the column generation algorithm 210 can begin with an empty set of beams, select one beam (e.g. a beam that has the highest potential to improve the current solution), add it to the "treatment set" or "solution set", and solve the FMO for the beam. In some embodiments, the FMO can be solved with a Chambolle-Pock algorithm or any other first-order primal-dual proximal-class algorithm.

In some embodiments, a column generation algorithm 210 can be used to approximate a BOO problem. A full BOO problem can theoretically involve all possible candidate beams to treat a patient (e.g. up to 180 beams, each at a different angle). However, this may not be physically feasible as it would be costly to deliver such large amounts of radiation and it could reduce the quality of life of a patient due to the extent of radiation exposure. Therefore, column generation can be used to approximate a solution with a limited number of beams. The column generation algorithm 210 can approximate the solution by iteratively adding beams one at a time to a "solution set" until a desired number of beams is reached (e.g. five or ten). During each iteration, the algorithm can calculate a fitness value for each possible beam based on an optimality condition of the objective function shown in Equation 1, $$_x^{min} \tfrac{1}{2} \Sigma_{\forall s \in S} \omega_s^2 \|D_s x - p\|_2^2 \, s \cdot t \cdot x \geq 0 \qquad (1)$$

where $\omega_s$ is the weight for structure s, which can be pseudo randomly generated between zero and one during a training process to generate many different scenarios. The p can be the prescription dose for each structure, which can be assigned one for the PTV and zero for OARs. D can be a dose influence matrix. At each iteration of the column generation algorithm 210, fitness values 214 can be calculated based on Karush-Kuhn-Tucker (KKT) conditions. In some embodiments, the KKT conditions can represent how much improvement each beam can make in the objective function (Equation 1) and can be derived from the Lagrangian of the system. In some embodiments, the beam with the highest fitness value can be selected to be added to the solution set, S. Then, FMO for the selected beams can be performed, which can affect the fitness value calculations for the next iteration. In some embodiments, the iterations are performed until the desired number of beams is in the solution set. In some embodiments, possible KKT conditions can include stationarity conditions, primal feasibility conditions, dual feasibility conditions, and/or complementary slackness (see Table 1). In some embodiments, the fitness value can be inversed and normalized to remain between zero and one; the larger the fitness value (e.g. a fitness value of one), the better the associated beam can be for improving the objective value at the next iteration. In some embodiments, an argmax function can be used to find a local maximum of the fitness value function (which plots the fitness value as a function of beam angle or orientation, see FIG. 8) and thus the corresponding beam angle. In other words, at each "iteration", the column generation algorithm 210 can receive inputs and generate a fitness value plot as a function of beam angle. In some embodiments, the beam angle corresponding to a maximum in the fitness value function can be determined (e.g. with an argmax function or any other similar function for finding mathematical maxima), and that beam can be added to the solution set as a selected beam.

Additional details on the column generation algorithm and KKT conditions are described in "A Fast Deep Learning Approach for Beam Orientation Optimization for Prostate Cancer Treated with Intensity-Modulated Radiation Therapy" by Barkousaraie et al. (2019), which is herein incorporated by reference in its entirety and attached hereto as Appendix I.

Framework 200 can be used to train supervised learning network 212 to generate predicted fitness values 216 that are comparable to or as close as possible to the fitness values 214 calculated by the column generation algorithm 210. In some embodiments, a loss function 218 can be used to evaluate the error of the predicted fitness values 216 in relation to the calculated fitness values 214. The network can learn to reduce the loss function and generate more accurate results (e.g. results with less error). In some embodiments, the loss function can be a Mean Squared Error (MSE) function and can include an Adam optimizer with a learning rate of $1 \times 10^{-5}$. In some embodiments, back-propagation 220 can compute the gradient of the loss function 218 with respect to the weights (not structure weights 206) of the neural network. In some embodiments, to train the network 212, a six-fold validation technique can be used (although any number can be used). In some embodiments, each fold can have a number of patient training data sets. In some embodiments, five of the folds can have a first number of validation patient training sets (e.g. ten), and the other fold can have a second number of validation patient training sets (e.g. seven). In some embodiments, a validation set for a fold can be a rolling set of patients (e.g. of size ten) which can vary from one fold to the next.

In some embodiments, folds can be trained over four hundred epochs. In some embodiments, each epoch can be trained with a step size of 2500. In a fold, the model with the least validation loss can be chosen and evaluated over a test data set. To evaluate the performance of the network 212, a model can be tested for one-on-one prediction (e.g. the same method used for training). In some embodiments, the average loss function can be used to measure the model of each fold's performance. Additionally, for each model (e.g. each fold), sets of five beams were generated and the resulting FMO was solved. In some embodiments, the FMO solution of each model can be compared with the solution generated by the column generation algorithm 210 for the same inputs. In some embodiments, various metrics can be used to compare a solution from the network 212 with the column generation algorithm 210, such as 1) the dose that 98% and 99% of the PTV receive ($D_{98}$ and $D_{98}$ respectively) 2) the maximum dose received by the PTV ($D_{max}$) 3) the homogeneity of the radiation received by the PTV, such as the difference between the dose received by 2% and 50% of the PTV 4) the Van't Riet conformation number (e.g. the volume of the PTV that received 100% of the dose) and 5) the volume of the PTV that received 50% of the dose ($R_{50}$). Example metrics are shown in Table 2. These metrics can be used to evaluate relative efficacy of a final treatment plan for selected beam sets.

Figure 3:
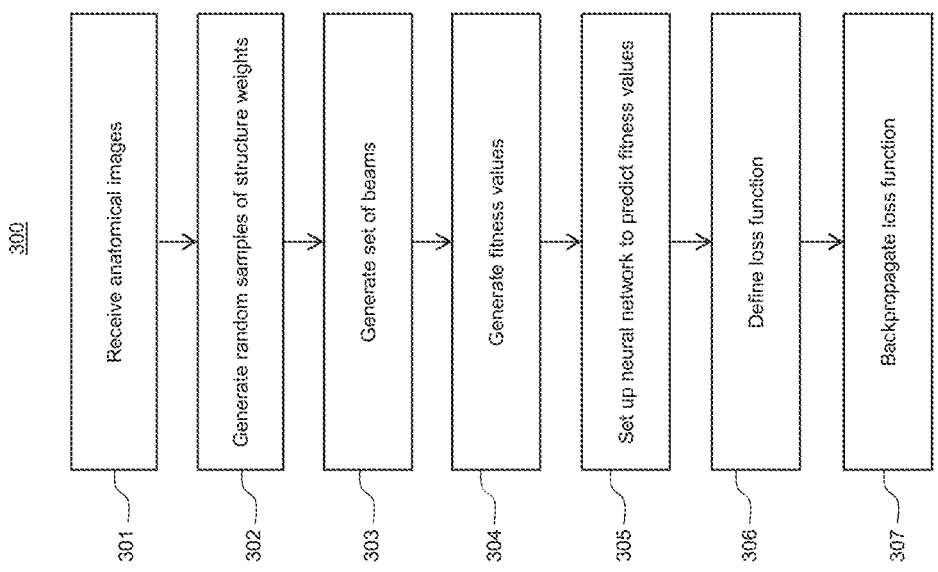
FIG. 3 is a process for training a neural network architecture to predict beam fitness values, according to some embodiments of the present disclosure.

FIG. 3 is a process 300 for training a neural network architecture to predict beam fitness values, according to some embodiments of the present disclosure. In some embodiments, process 300 may be performed by a computer or other computing device. At block 301, a computer may receive anatomical images for a plurality of patients. In some embodiments, anatomical images can include images of tumors and organs/tissue surrounding the tumor in each patient. In some embodiments, the images can include contours, where the contours may reflect different organs of types of tissue (e.g. bladder, body, rectum, PTV, other OARs, etc.). At block 302, random samples of structure weights can be generated. In some embodiments, this can be used to generate a large training dataset. Random samples of structure weights can be generated for each set of anatomical images and be assigned to the contoured organs within the images, similar to or the same as described in relation to framework 200. At block 303, a set of beams for each input set of data (e.g. each set of anatomical images and associated structure weights) can be selected. In some embodiments, the set of beams can be selected via a column generation algorithm or any other beam orientation optimization algorithm that can involve fitness values or optimality conditions.

At block 304, the fitness values can be generated for each set of beams selected at block 303. In some embodiments, fitness values may be based on optimality conditions, such as KKT conditions. In some embodiments, the KKT conditions can be used to determine which single beam would best improve the objective function at the next iteration (Equation 1). KKT conditions are generally used to evaluate whether a solution is optimal; in other words, if all KKT conditions are met for a solution, then the solution can be considered optimal. In some embodiments, to obtain the KKT conditions, the Lagrangian for the master FMO problem of a set of beam angles can be written as $$L(x, y, z, v) = F(y) + \left\langle z, \sum_{b \in B} \left( \begin{bmatrix} D_{b,s=s_1} \\ \vdots \\ D_{b,s=s_T} \end{bmatrix} x_b \right) - y \right\rangle - \sum_{b \in B_{all}} \langle v_b, v_x \rangle \quad (2)$$

where z and v≥0 can be Lagrange multipliers, F can be the objective function, x is the intensity array of a candidate beam b of the set of selected beams (B), s is the set of available structures (e.g. OARs, PTV, and tuning structures), and D is the dose influence matrix. In some embodiments, the KKT conditions derived from Equation 2 can be divided into four categories, shown in Table 1.

TABLE 1

| KKT Condition | |
|---|---|
| Stationarity | $v_b = \begin{bmatrix} D_{b,s=s_1} \\ \vdots \\ D_{b,s=s_T} \end{bmatrix}^T Z$ for $b \in B_{all}$ |
| | $z \in \partial F(y)$ |
| Primal Feasibility | $y = \sum_{b \in B} \begin{bmatrix} D_{b,s=s_1} \\ \vdots \\ D_{b,s=s_T} \end{bmatrix} x_b$ |
| Dual Feasibility | $x_b \geq 0$ for $b \in B_{all}$ |
| | $v_b \geq 0$ for $b \in B_{all}$ |
| Complementary Slackness | $v_{b,i} x_{b,i} = 0 \quad \forall b, i$ |

In some embodiments, for many, if not all, possible beam orientations, the dual feasibility conditions may not be met. When solving the FMO problem using a primal-dual algorithm (e.g. as described in relation to the column generation discussion in FIG. 2), ∂F(y) can be calculated. From here, all $v_b$ can be calculated using the stationarity condition (e.g. of Table 1). The corresponding beam orientation or angle where the value $\Sigma_i(v_{b,i})$ is the most negative (e.g. the furthest from meeting the dual feasibility optimality condition) can improve the objective function (Equation 1) the most if added to the total set of beams. If $$r_b = -\Sigma_i(v_{b,i}) \quad (3)$$

where $r_b$ can represent the possible improvement in the objective function by adding a beam b to the set of selected beams, a fitness vector, f, can be defined as $$f = \frac{\begin{bmatrix} r_{b=b_1} \\ \vdots \\ r_{b=b_J} \end{bmatrix} - \min(r)}{\max(r) - \min(r)}. \quad (4)$$

In some embodiments, the fitness can be normalized from zero to one, which can be set up for training the neural network. In some embodiments, the larger the value of the fitness (Equation 4), the better the associated beam can be for improving the objective value (Equation 1).

In some embodiments, the fitness values can be generated according to the methods described in "A Fast Deep Learning Approach for Beam Orientation Optimization for Prostate Cancer Treated with Intensity-Modulated Radiation Therapy."

At block 305, a neural network architecture can be configured to predict fitness values for beam angles based on anatomical input data. At block 306, a loss function can be defined as the error between the fitness values generated in block 304 and the predicted fitness values in block 305. At block 307, the loss function can be backpropagated to the neural network; this can "train" the neural network to generate more accurate results. In some embodiments, the loss function can be a Mean Squared Error (MSE) function and can include an Adam optimizer with a learning rate of $1 \times 10^{-5}$. In some embodiments, block 307 can compute the gradient of the loss function 306 with respect to the weights/parameters of the neural network. In some embodiments, a six-fold validation technique can be used (although any number can be used) to train the network.

Figure 4:
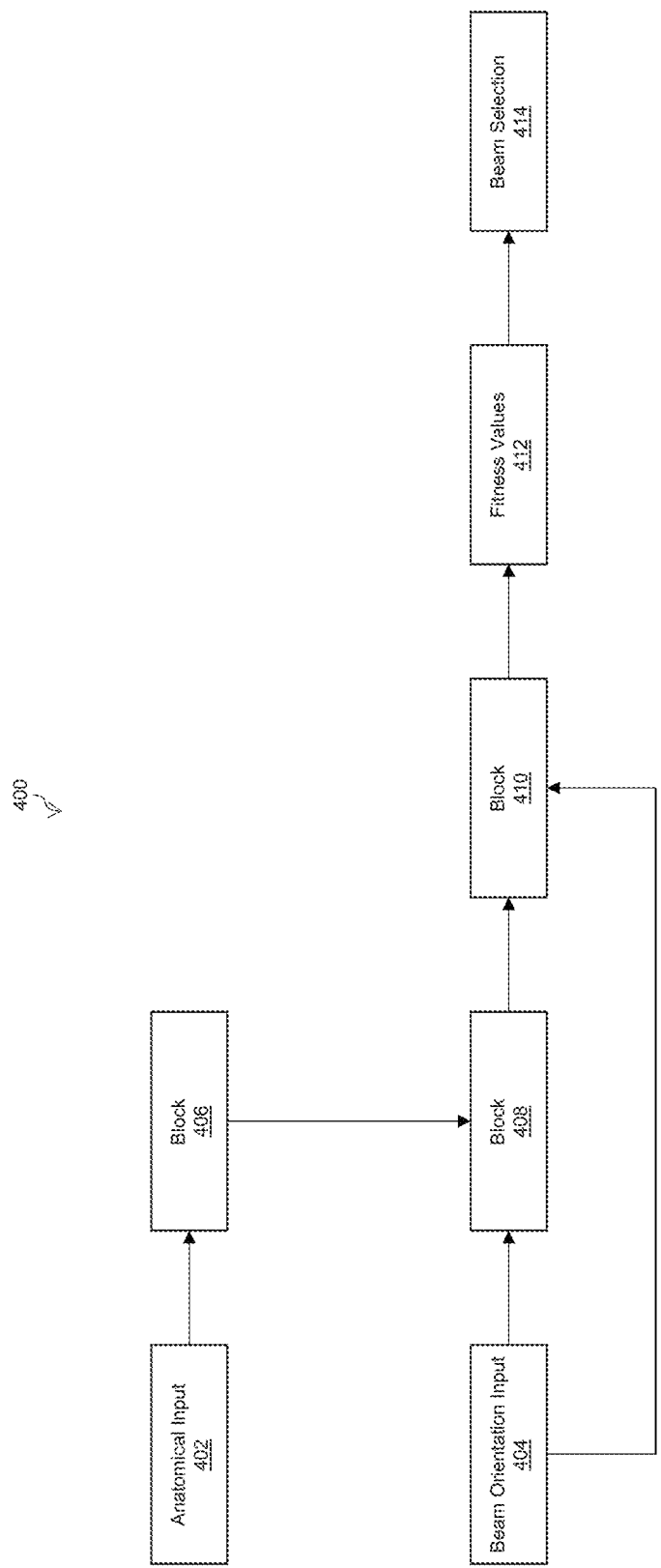
FIG. 4 is an illustrative neural network architecture for predicting beam fitness values, according to some embodiments of the present disclosure.

FIG. 4 is an illustrative neural network architecture 400 for predicting beam fitness values, according to some embodiments of the present disclosure. In some embodiments, the architecture 400 can be used to consecutively predict a number of beams for a patient based on input data (e.g. five beams). The architecture 400 can receive two inputs: anatomical input 402 and beam orientation input 404. In some embodiments, anatomical input 402 can include images (e.g. contoured images) of a patient's anatomy. In some embodiments, the images can be images of a tumor and of OARs surrounding the tumor. In some embodiments, the anatomical input 402 can include OAR structure weights (e.g. structure weights 206 of FIG. 2). In some embodiments, anatomical input 402 can be in the form of target and avoidance matrices. In some embodiments, anatomical input 402 can include two channels, each of size 64×64×64. The first channel can represent the PTV as a target channel, and the second channel can represent weighted OARs as an avoidance channel. In some embodiments, the channels can have data similar to binary masks of the structures, but the PTV and OARs, respectively, can be assigned nonzero values. The nonzero values can be the structure weighting of the OARs. In some embodiments, the beam orientation input 404 can include a Boolean array of size 180 (e.g. the number of candidate beam orientations at 2-degree resolution). In some embodiments, each element of the array can be associated with one candidate beam. The beam orientation input 404 can represent beam orientations that are already chosen as "ones" and the rest as "zeros". In some embodiments, the beam orientation input 404 can initially be an array of all zeros, meaning no beams have been selected. As a beam is selected by the network, the element in the array corresponding to that beam can be changed to a "one."

In some embodiments, block 406 can analyze the anatomical input 402 using three-dimensional convolutional layers. In some embodiments, convolutional layers can make a locality assumption that adjacent data can be related to each other (e.g. a beam of zero degrees and a beam of two degrees are more similar than zero degrees and eight degrees). In some embodiments, convolutional layers can learn how to internalize this. The output of block 406 can be a layer with a smaller number of features (e.g. 1024). Additional details on the processing within block 406 are described in FIG. 5. In some embodiments, block 408 can analyze both the beam orientation input 404 and the output of block 406. Block 408 can combine the anatomy layer (received from block 406) and the beam orientation input 404. Additional details of the processing within block 408 are described in FIG. 6. In some embodiments, block 410 can receive and analyze the output from block 408 and beam orientation input 404 and output fitness values 412. In some embodiments, fitness values 412 can be a feature array of size 180, which can represent the fitness values of candidate beam orientations (e.g. based on the dual feasibility KKT conditions as described in relation to FIG. 2). In some embodiments, beam selection 414 can evaluate the fitness values 412 to select a beam angle. In some embodiments, beam selection 414 can be configured to utilize an argmax function. In some embodiments, to the extent it is desired to obtain a set of multiple beams as a solution set, once a beam is selected at beam selection 414, it can be added to the beam orientation input 404 (e.g. by adding a "one" to the element associated with that beam angle in the array). From here, the network architecture 400 can be run again to select the next beam to add to the solution set. The architecture 400 can be run iteratively to select any desired number of beams for a treatment plan. In some embodiments, the activation function of layers in the network architecture 400 (layers are described in further detail in FIGS. 5-7) can be Scaled Exponential Linear Unit (SELU). SELU is a self-normalizing activation function that can converge to zero mean and unit variance even in the presence of noise. However, additional activation functions may be used.

Figure 5:
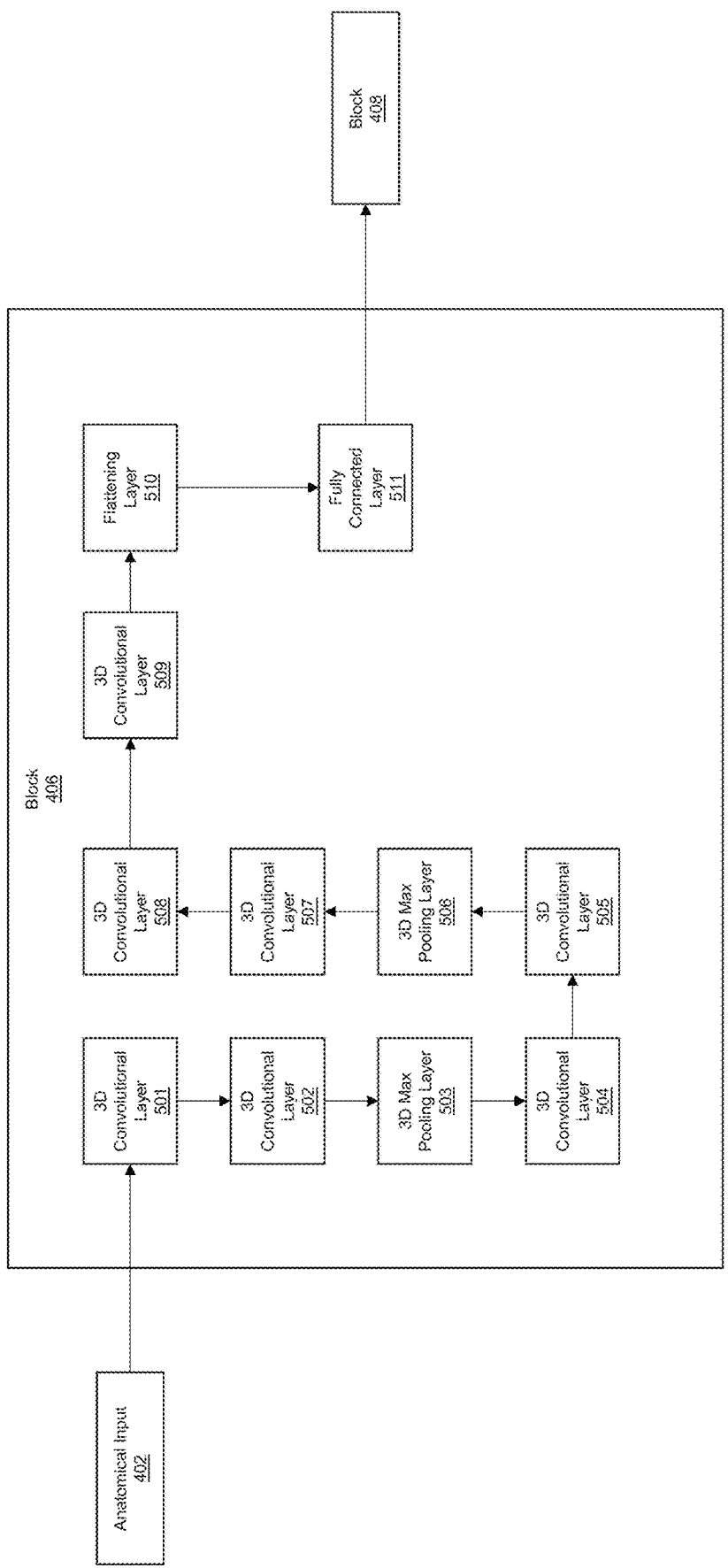
FIG. 5 is an illustrative block that can be used within the neural network architecture of FIG. 4, according to some embodiments of the present disclosure.

FIG. 5 is an illustrative block 406 that can be used within the neural network architecture 400 of FIG. 4, according to some embodiments of the present disclosure. In some embodiments, block 406 can receive anatomical input 402 (e.g. the anatomical input 402 of FIG. 4). In some embodiments, block 406 can process the anatomical input 402 with two 3D convolutional layers 501 and 502, followed by a 3D max pooling layer 503. Convolutional layers 501 and 501 can be configured to perform convolution (e.g. convolve with multiplication or an inner product) on the anatomical input 402 and the convolutional layers can include sets of learnable filters (e.g. kernels). In some embodiments, convolutional layers 501 and 502 can include 5×5×5 kernel sizes. The 3D max pooling layer 503 can reduce the dimension of the output received from convolutional layer 502. In some embodiments, max pooling layer 503 can be of size 2×2×2. In some embodiments, the output of max pooling layer 503 can be received and analyzed by additional 3D convolutional layers 504 and 505. In some embodiments, convolutional layers 504 and 505 can also include kernel sizes of 5×5×5. 3D max pooling layer 506 can receive the output from convolutional layer 505 to further reduce the dimension. In some embodiments, max pooling layer 506 can also be of size 2×2×2. In some embodiments, the output of max pooling layer 506 can be processed by three consecutive 3D convolutional layers 507-509. Convolutional layers 507-509 can each have a kernel of 3×3×3. In some embodiments, the output from the consecutive convolutional layers can be processed by a flattening layer 510. Flattening layer 510 can flatten the data to one-dimensional layer (e.g. of 8192 elements). In some embodiments, a fully connected layer 511 can process the output of the flattening layer 510 to reduce the data to 1024 features. In some embodiments, the output of the fully connected layer can be processed by block 408.

Figure 6:
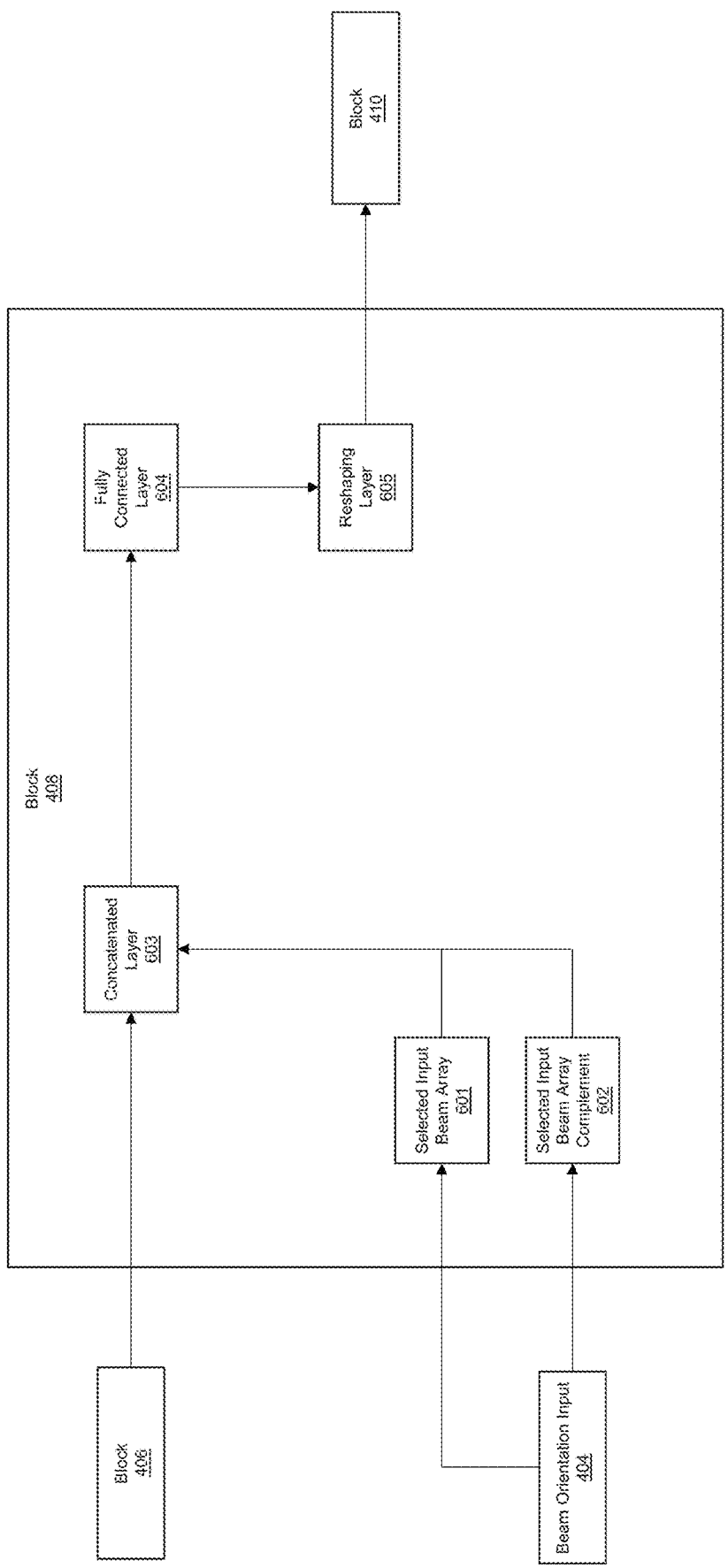
FIG. 6 is another illustrative block that can be used within the neural network architecture of FIG. 4, according to some embodiments of the present disclosure.

FIG. 6 is another illustrative block 408 that can be used within the neural network architecture 400 of FIG. 4, according to some embodiments of the present disclosure. Block 408 can receive the output of block 406 (e.g. a layer of 1024 features from fully connected layer 511) and the beam orientation input 404. Block 601 can process the beam orientation input 404 into an array of size 180. Block 602 can process the beam orientation input 404 into the complementary array of the array generated at block 601 (e.g. the complementary array can also be of size 180). In some embodiments, using complementary Boolean arrays can enhance the influence of already selected beam orientations on the neural network. A concatenated layer 603 can process the 1024 feature array from block 406, the beam array from block 601, and the complementary beam array from block 602. In some embodiments, the concatenated layer 603 can add the inputs to generate data of size 1384. The output of concatenated layer 603 can be processed by a fully connected layer 604. In some embodiments, fully connected layer 604 can generate an output of size 5120 features. The output of fully connected layer 604 can be processed by reshaping layer 605 to reshape to output into a different format. For example, reshaping layer 605 can reshape a layer of 5120 features into five rows of 1024 features. In some embodiments, the output of the reshaping layer 605 can be processed by block 410.

Figure 7:
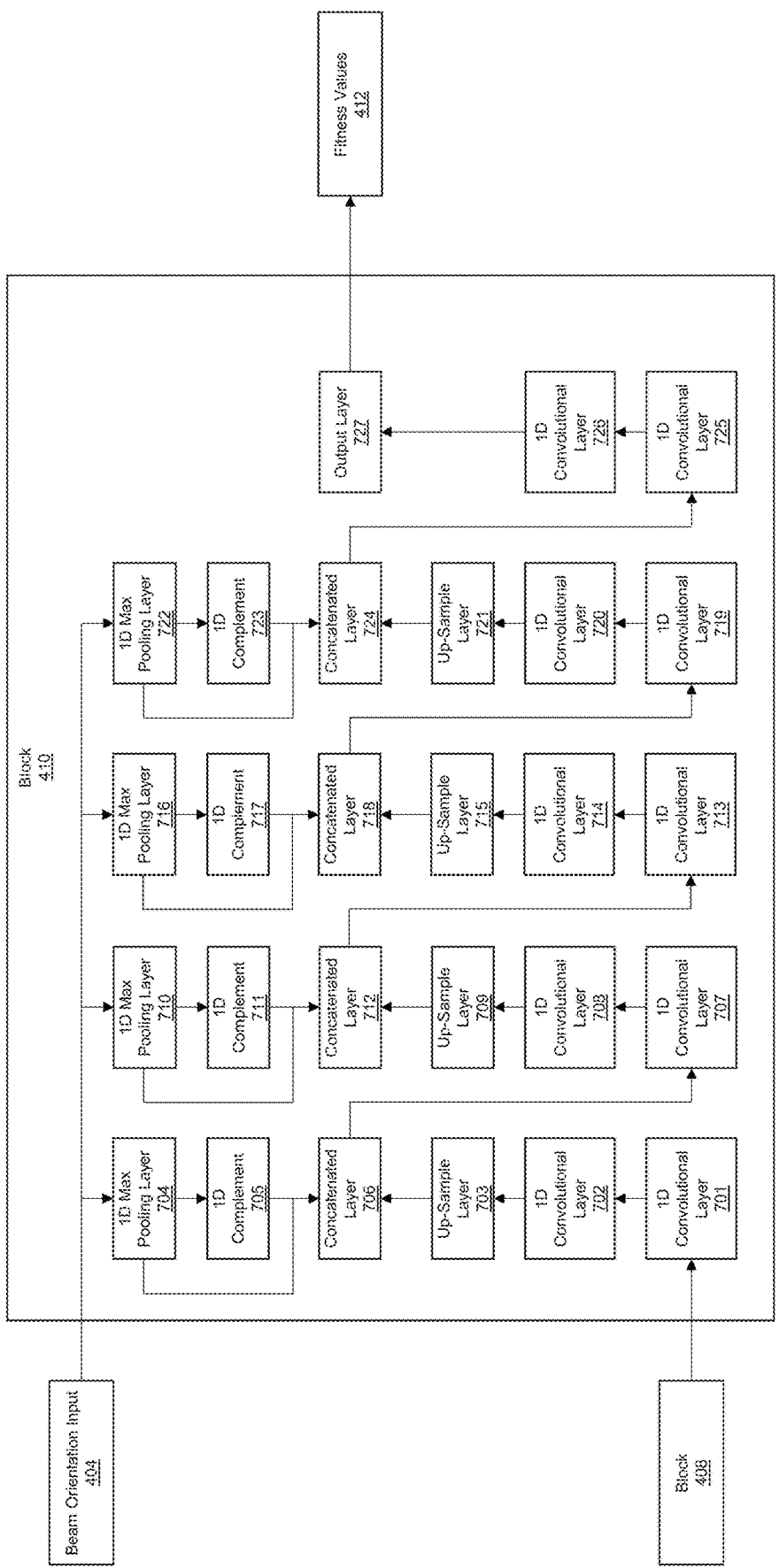
FIG. 7 is another illustrative block that can be used within the neural network architecture of FIG. 4, according to some embodiments of the present disclosure.

FIG. 7 is another illustrative block 410 that can be used within the neural network architecture 400 of FIG. 4, according to some embodiments of the present disclosure. In some embodiments, block 410 can be referred to as an up-sampling stage and may utilize a convolutional approach (e.g. employs convolutional layers instead of fully connected layers). In some embodiments, block 410 can receive the beam orientation input 404 and the output from block 408 (e.g. five rows of 1024 features). In some embodiments, block 410 can include five stages. Each stage can begin with two consecutive 1D convolutional layers (e.g. 1D convolutional layers 701/702, 707/708, 713/714, 719/720, and 725/726 respectively at each stage). The convolutional layers can receive and process the output from block 408. In some embodiments, each convolutional layer can include a kernel of size 3. In some embodiments, the output of the convolutional layers 701 and 702 can be processed by an up-sample layer 703 (or 709, 715, and 721 respectively at each stage) to increase the dimension. Beam orientation input 404 can be processed by a 1D max pooling layer 704 (or 710, 716, and 722, respectively at each stage) to reduce the dimension of the beam orientation data. In some embodiments, a concatenated layer 706 (or 712, 718, and 724, respectively at each stage) can add the complement of beam orientation 705 (or 711, 717, and 723 respectively at each stage), the output from the up-sampling layer 703, and the output of the max pooling layer 704. In some embodiments, this processing can be performed at each stage until it reaches 1D convolutional layer 726. In some embodiments, convolutional layer 726 can be configured to output a feature array reflecting fitness values 412 (e.g. of size 180) at output layer 727. In some embodiments, the feature array can represent the dual values of candidate beam orientations. Note, in some embodiments, the pool size of each 1D max pooling layer can dynamically change based on the size of the current stage's data. For example, max pooling layer 704 can have a pooling size of twelve, max pooling layer 710 can have a pooling size of four, max pooling layer 716 can have a pooling size of two, and max pooling layer 722 can have a pooling size of one. In some embodiments, the dual value of beams (e.g. fitness values 412) can show the potential improvement in the current state of the problem (e.g. the value of the objective function, Equation 1) if a beam is added to the current set of selected beams. In some embodiments, the inversed and normalized dual array can be used as a probability distribution of beam orientation selection. In some embodiments, the five stages within block 410 can be replaced with five fully connected layers.

Figure 8:
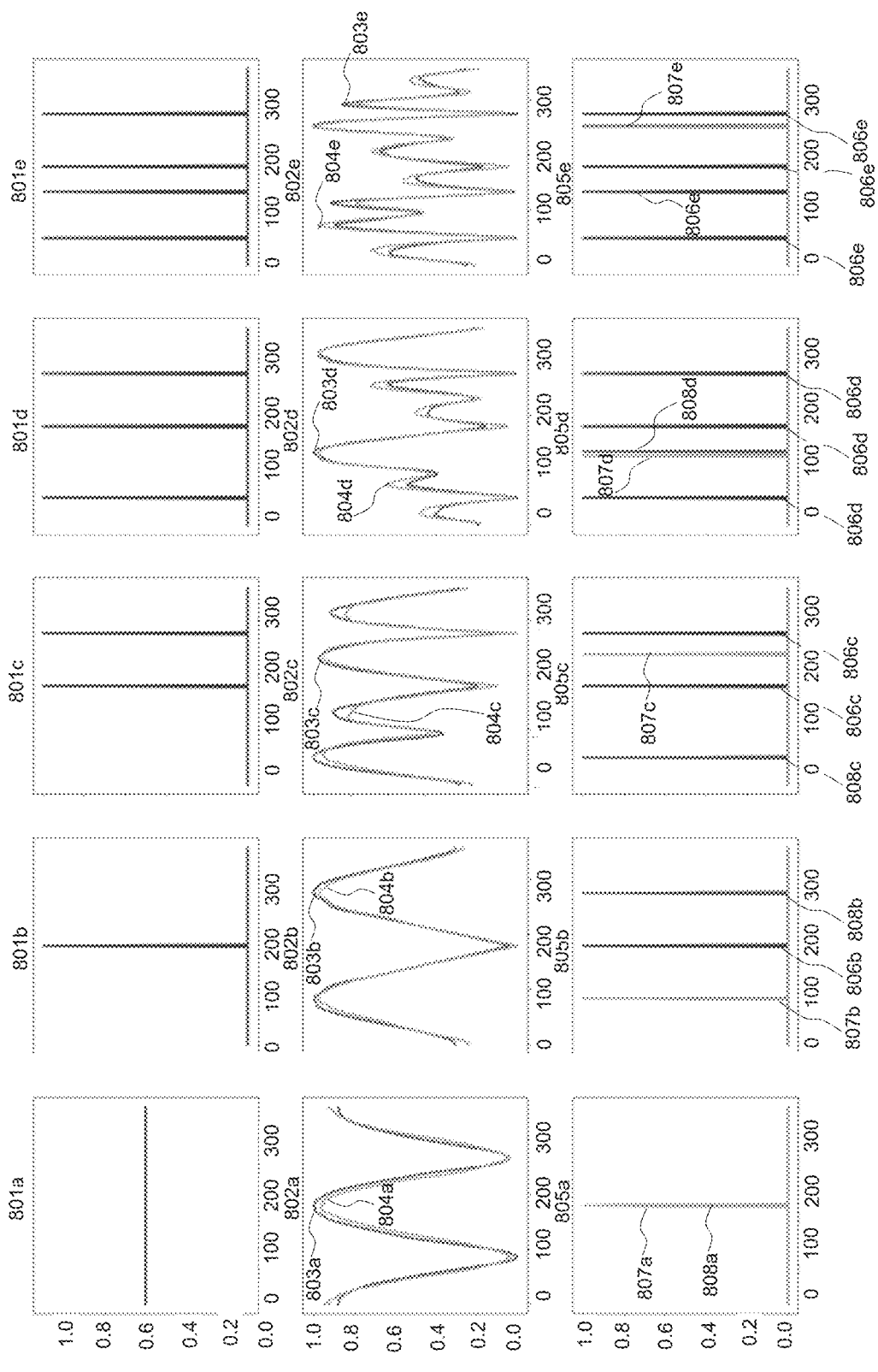
FIG. 8 shows prediction results for a neural network architecture, according to some embodiments of the present disclosure.

FIG. 8 shows prediction results for a neural network architecture, according to some embodiments of the present disclosure. Each column of plots (e.g. 801*a*-805*a*, 801*b*-805*b*, etc.) can represent an iteration of neural networking processing, such as described in FIG. 4. Plots 801*a*-*e* (the top row of plots) indicate the set of already selected beam orientations. In other words, each plot 801 indicates initially selected beams, similar to or the same as beam orientation input 404 of FIG. 4. Plots 802*a*-*e* (middle row) indicate the fitness values of beams for a test patient, both for a column generation method and a neural network method. Plots 805*a*-*e* (bottom row) depict the updated set of beam orientations based on the input beams and argmax of fitness value, both for column generation and a neural network method.

Plot 801*a* may indicate that the original set of selected beam orientations is null (e.g. no beams selected). The x-axis of all plots in FIG. 8 is beam angle with a range of 0 to 180 degrees. Plot 802*a* may indicate a plot of the fitness values for all possible beam candidates for an example patient. Line 803*a* is a column generation solution; line 804*a* is a neural network solution, according to some embodiments herein. For example, line 804*a* may have been generated using the neural network architecture 400 of FIG. 4 and/or the methods of FIG. 9. Plot 805*a* can indicate a beam angle selected based on the fitness value function in plot 802*a*. Plot 805*a* can include beam angle selections 807*a* and 808*a*. In some embodiments, beam angle 807*a* may have been chosen by a neural network architecture and beam angle 808*a* may have been chosen by a column generation algorithm. Note in plot 805*a*, the beam angle chosen by both methods was about the same. The mean square error for plot 805*a* is 0.354%.

The beam angle selected in plot 805*a* can be added to the solution set of selected beams and re-processed by both the column generation algorithm and the neural network. Plot 801*b* shows the currently selected beams, the same beam chosen in plot 805*a*. In other words, the beam chosen in plot 805*a* is now an input beam orientation data. In plot 802*b*, the fitness value functions for column generation (803*b*) and the neural network (804*b*) are shown. In plot 805*b*, the input beam is shown (806*b*), along with the next selected beam according to column generation (808*b*) and the neural network (807*b*). The mean square error 805*b* is 0.110%.

The beam angle selected in plot 805*b* can again be added to the solution set of selected beams and re-processed by both the column generation algorithm and the neural network. Plot 801*c* shows the currently selected beams, the same beam chosen in plot 805*b*. In other words, the beam chosen in plot 805*b* is now an input beam orientation data. In plot 802*c*, the fitness value functions for column generation (803*c*) and the neural network (804*c*) are shown. In plot 805*c*, the input beams are shown (806*c*), along with the next selected beam according to column generation (808*c*) and the neural network (807*c*). The mean square error for plot 805*c* is 0.333%.

The beam angle selected in plot 805*c* can again be added to the solution set of selected beams and re-processed by both the column generation algorithm and the neural network. Plot 801*d* shows the currently selected beams, the same beam chosen in plot 805*c*. In other words, the beam chosen in plot 805*c* is now an input beam orientation data. In plot 802*d*, the fitness value functions for column generation (803*d*) and the neural network (804*d*) are shown. In plot 805*d*, the input beams are shown (806*d*), along with the next selected beam according to column generation (808*d*) and the neural network (807*d*). The mean square error in plot 805*d* is 0.241%.

The beam angle selected in plot 805*d* can again be added to the solution set of selected beams and re-processed by both the column generation algorithm and the neural network. Plot 801*e* shows the currently selected beams, the same beam chosen in plot 805*d*. In other words, the beam chosen in plot 805*d* is now an input beam orientation data. In plot 802*e*, the fitness value functions for column generation (803*e*) and the neural network (804*e*) are shown. In plot 805*e*, the input beams are shown (806*e*), along with the next selected beam according to column generation (808*e*) and the neural network (807*e*). Plot 805*e* can show a full set of selected beam angles for a treatment plan (e.g. five total beam angles). The mean square error is 0.339%. Note, in some embodiments, the neural network may choose a different beam orientation than the column generation algorithm in the presence of multiple local optimums. In some embodiments, this may be because there can be several beam orientations within a small distance of the minimum (maximum in the plots due to a negative) dual values. However, the quality of solutions of column generation vs. the neural network, even if different beams are selected, should be the same or comparable.

Figure 9:
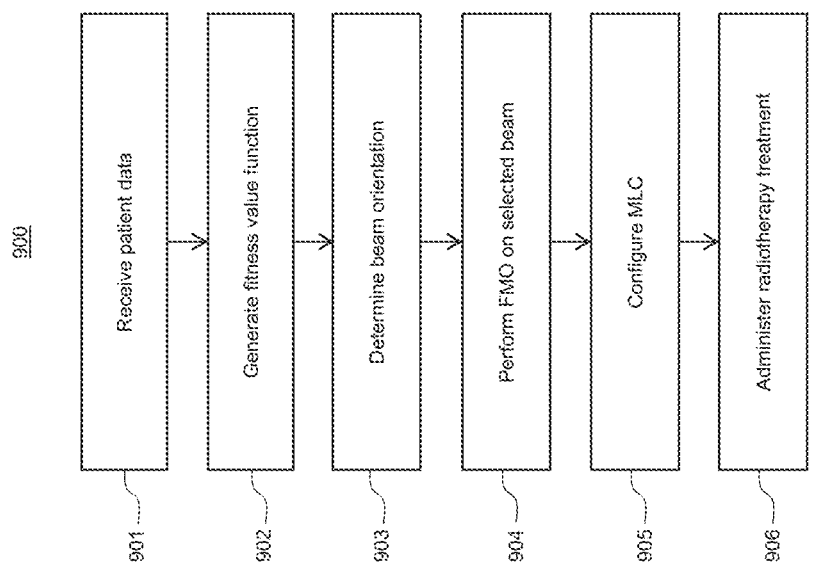
FIG. 9 is a process for using a neural network architecture to select beam orientations for a radiotherapy plan, according to some embodiments of the present disclosure.

FIG. 9 is a process 900 for using a neural network architecture to select beam orientations for a radiotherapy plan, according to some embodiments of the present disclosure. In some embodiments, process 900 can be performed by computing device 114 of FIG. 1. At block 901, computing device 114 can receive patient data (e.g. anatomical input 402 of FIG. 4). In some embodiments, patient data can include images of a patient's anatomy. In some embodiments, the images can be contoured, the contours reflecting different regions and/or volumes within the body. Regions can include PTV (e.g. the tumor) and various OARs (e.g. rectum, bladder, etc.). In some embodiments, patient data can also include structure weights for OARs, as described in relation to FIG. 2. In some embodiments, patient data can be received as an input to a neural network architecture and can be in the form of target and avoidance matrices and/or target and avoidance channels. In some embodiments, process 900 can also begin with a beam orientation input: the beam orientation input may depend on a physician or dosimetrist's desired choice of beams. In some embodiments, this may be zero, and the beam orientation input can be an empty set (e.g. a Boolean array of 180 zeros). In some embodiments, a physician may select any number of beams to begin and the beam orientation input may reflect this.

At block 902, computing device 114 can generate a fitness value function. In some embodiments, the fitness value function may be generated using a neural network architecture (e.g. network architecture 400 of FIG. 4). In some embodiments, the neural network architecture may receive the patient data as an input and may analyze the patient data with one or more convolutional layers. In some embodiments, the neural network architecture may generate fitness values for all possible beam candidates (e.g. all possible beam angle candidates, such as degrees 0 through 180 with 2 degrees separation). In some embodiments, the fitness values may be based on optimality conditions (e.g. dual feasibility KKT conditions) predicted by the neural network architecture. In some embodiments, processing at block 902 may include analyzing the patient data with the neural network architecture described in FIGS. 4-7. In some embodiments, the output of the neural network architecture in block 902 may be an array of size 180 (or whichever size is deemed necessary based on the possible beam candidates for the type of radiotherapy), which element in the array containing a fitness value for the associated beam angle. In some embodiments, the fitness value can be normalized to remain between zero and one. In some embodiments, the fitness values can be inversed.

At block 903, computing device 114 can determine a beam orientation. In some embodiments, computing device 114 can be configured to plot the elements of the output array from block 902 on a two-dimensional chart or can just analyze the array in two-dimensions. The two dimensions can refer to the number element of the array (which can correspond to a beam angle, e.g. element six can correspond to a beam angle of six degrees) and the predicted fitness value in that array. In some embodiments, determining a beam orientation from the fitness value function or array can include using an argmax function to find a local maximum value of the fitness value function. In some embodiments, the beam angle corresponding to the local maximum value of the fitness value function can be selected as a beam angle.

In some embodiments, determining a beam orientation based on the fitness value function can include using a tree search algorithm. In some embodiments, a tree search algorithm can be used to explore the decision space of beam orientations and their predicted fitness values. In some embodiments, the neural network architecture can be used to guide the traversal of the branches of a Monte Carlo decision tree to select a new beam to the treatment plan. In some embodiments, utilizing a tree search in accordance with the trained neural network architecture of the present disclosure can provide the probability of selecting a beam in the search space of the tree, so that the beam with the better likelihood to improve the objective function (Equation 1) has the higher chance of being selected. As described herein, a decision tree can refer to the solution space of a set of discrete numbers (e.g. the discrete numbers are the beam orientations/angles) and a node and a branch can represent the selection of one number or a subset of available numbers, respectively. In some embodiments, each branch of the tree of the neural network can start from a root (e.g. a node with an empty set of beam angles) as an empty set of beams and can continue until it reaches the number of desired beams in the solution set (e.g. as chosen by a user or physician). After the exploration of each complete treatment plan (e.g. selection of five radiation beam angles), the FMO problem can be solved for the selected angles and, based on the FMO, the probability distribution to select the next beam can be updated. A tree search can explore the decision space by randomly sampling from it. In some embodiments, a tree search algorithm can, at each node (e.g. selection of one potential beam orientation), starting with a root, use the neural network to predict an array of fitness values for each beam orientation. This can be performed until it reaches the end of the tree (e.g. the final beam angle). In some embodiments, each element in this array can represent the likelihood of the selection of the associated beam orientation. For example, if the number of potential beams is 180 with two-degree separation, the array would be of size 180 and the probability of selecting a beam orientation in the second position of the array would be the probability of selecting a beam angle of four degrees.

In some embodiments, an expansion process can occur after selecting nodes to further explore the tree and create children nodes, which can represent subsequent actions or decisions in the tree search. In some embodiments, the creation of a child node can be done when the selected action or decision is initially an unexplored one. A branch created for a node can continue expanding until there are N+1 nodes in the branch (e.g. N+1=6 for a selected set of five beams). A branch with five nodes can refer to a treatment plan with five selected beam angles. In some embodiments, only one child node may be created at a time. In some embodiments, the problem can be defined as a dynamic programming problem with the formula $$G_k^s = S \cup \{k\} \cup G_{n*}^{S \cup \{k\}} \mid n^* = \genfrac{}{}{0pt}{}{\text{argmax}}{n > k} V_{G_n^{S \cup \{k\}}}. \tag{5}$$

In Equation 5, S can be a set of indices for previously selected beams, k can be an index of currently selected beams and $G_{n*}^{S \cup \{k\}}$ can be a subset of beams to be selected that has the highest reward value. In some embodiments, the reward value may be based on a reward function, which is a function of the node's cost values and the best cost value ever discovered in the search process and based on the FMO of nodes. Each "simulation" can include iteratively selecting a predefined number of beams (N). In some embodiments, after the exploration of each complete plan, the FMO can be solved and used for a backpropagation step, which can be used to update the probability distribution for beam selection.

In some embodiments, various tree search algorithms can be used to determine a beam orientation in block 903, such as a guided tree search (GTS), a guided search (GuidS), a randomly sampled tree search (RTS), or a random search (RandS). In some embodiments, a GuidS algorithm can use the neural network to search the decision space by iteratively choosing one beam based on the predicted probabilities from the network but does not update as the search progresses. In some embodiments, an RTS algorithm can use a simple Monte-Carlo tree search method which can start with a uniform distribution to select beam angles (e.g. randomly selecting angles), and then updating as the tree search progresses. Note the RTS algorithm does not use the neural network to guide the search. In some embodiments, a RandS algorithm can search the decision space of the neural network with uniform, random probability until a stopping-criteria is met. It can randomly select five beam angles and solve the corresponding FMO.

Additional details related to using search algorithms on conjunction with the neural network architecture of the present disclosure can be described in "A Reinforcement Learning Application of Guided Monte Carlo Tree Search Algorithms for Beam Orientation Selection in Radiation Therapy" by Sadeghnejad-Barkousaraie et al. (2020) which is herein incorporated by reference and attached hereto as Appendix II.

At block 904, computing device 114 can perform FMO on the beam selected in block 903, which can be used to develop radiation intensities for the actual treatment plan. At block 905, computing device 114, via control unit 112, can configure an MLC to administer a radiation beam in accordance with the FMO computed for the selected beam. At block 906, a radiotherapy treatment in accordance with the selected beam and FMO can be administered to a patient. In some embodiments, a dose distribution can be determined or calculated for a patient based on the FMO, and this dose distribution can be administered to the patient. In some embodiments, blocks 901-903 can be repeated any amount of times until the number of desired beams has been selected. For example, if a physician desires a treatment plan with five different beams, blocks 901-903 can be performed until five beams have been selected. From here, process 900 can proceed, only using a set of five beams instead of one. Note, after a beam has been selected, the beam orientation input data that is considered and processed by the neural network architecture to predict a beam is updated to reflect the currently selected beams.

Figure 10:
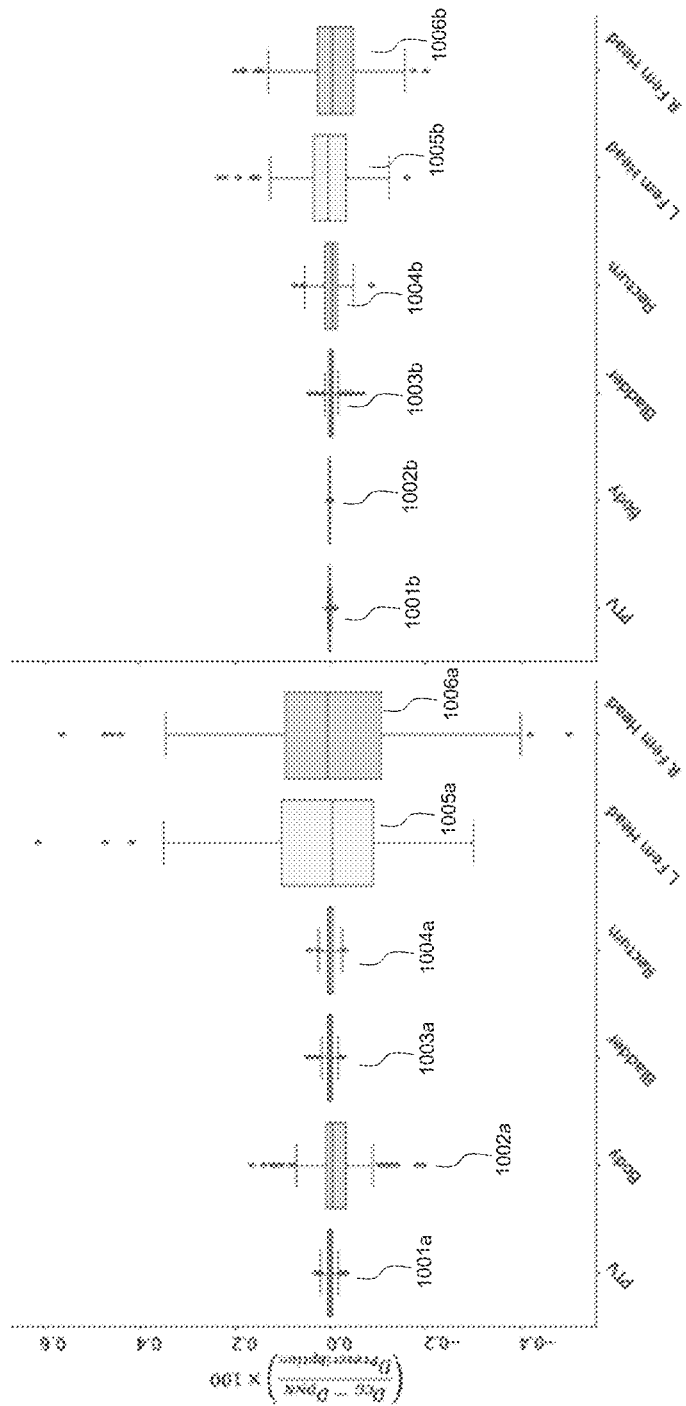
FIG. 10 shows dose difference percentages for a neural network architecture, according to some embodiments of the present disclosure.

FIG. 10 shows dose difference percentages for a neural network architecture, according to some embodiments of the present disclosure. In some embodiments, plots 1001a-1006a can represent the maximum dose difference percentages between final solutions of column generation and the neural network and plots 1001b-1006b can represent eh mean dose difference percentages between final solutions of column generation and the neural network. Note, the final solutions to the neural network approach and the column generation approach can be the final dose calculations resulting from solving the FMO problem for each set of selected beams. On average, the dose differences received by OAR were between one and six percent. Bladder (1003a-b) had the smallest average difference in dose received (0.96±1.18%). The rectum (1004a-b) had 2.44±2.11%, the left femoral head (1005a-b) had 6.03±5.86%, the right femoral head (1006a-b) had 5.89±5.52%, and the body (1002a-b) had 0.10±0.10% between the generated treatment plans. The difference between PTV dose 1001a-b is around 0.002±0.002%.

Figure 11:
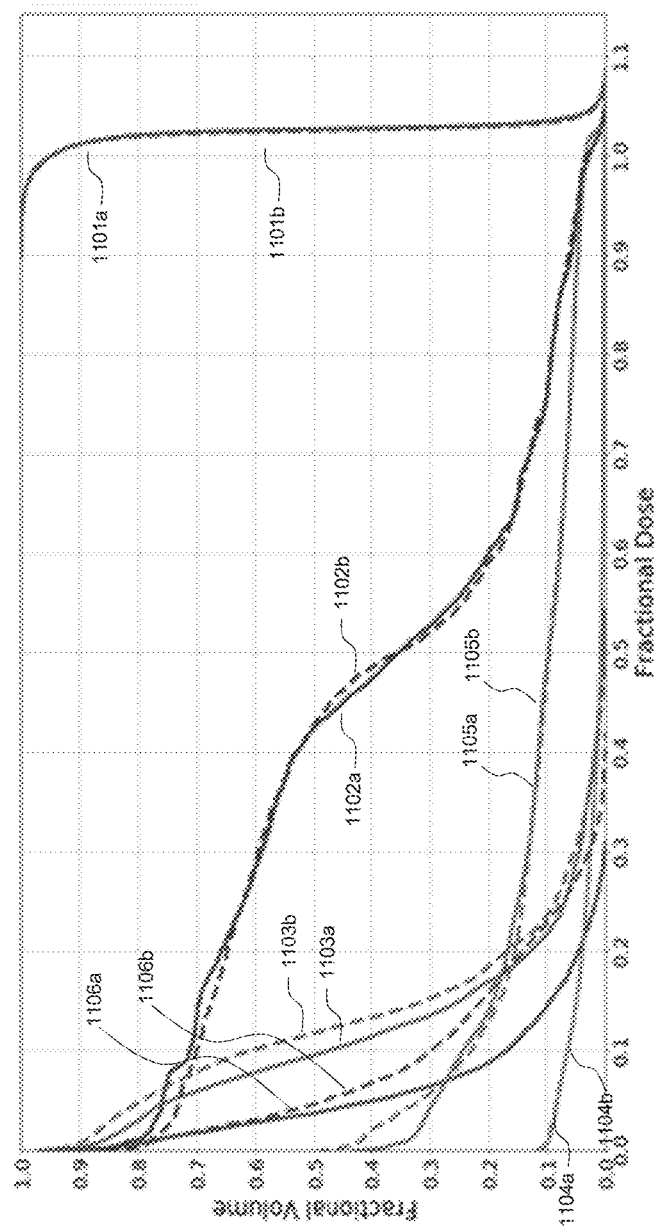
FIG. 11 shows dose volume histogram (DVH) information for a neural network architecture, according to some embodiments of the present disclosure.

FIG. 11 shows dose volume histogram (DVH) information for a neural network architecture, according to some embodiments of the present disclosure. In some embodiments, a DVH can be a reversed cumulative histogram of the dose distribution in a structure of interest, effectively reducing the 3-dimensional data to a 2-dimensional plot. In some embodiments, the DVH can be used by clinicians during the planning process to evaluate the quality of the plan, and to decide whether to approve or reject the plan. In some embodiments, a DVH can relate radiation dose to tissue volume and can be used in radiation therapy planning and can be determined after solving the FMO for each set of solutions. DVHs can compare doses from a treatment plans to different structures (e.g. the PTV and OARs). The x-axis of FIG. 11 is the fractional dose while the y-axis is the fractional volume. In some embodiments, the dashed lines can refer to the neural network solution and the solid lines can refer to the column generation solution. Curve 1101a (solid) and curve 1101b (dashed) show the DVH curse for the PTV and indicates noticeably more radiation is received by the PTV (e.g. prostate cancer) than the normal, non-cancerous organs surrounding the tumor in both methods. Curves 1102a (solid) and 1102b (dashed) show the DVH curves for the rectum, curves 1103a (solid) and 1103b (dashed) show the DVH curves for the left femoral head, curves 1104a (solid) and 1104b (dashed) show the DVH curves for the body, curves 1105a (solid) and 1105b (dashed) show DVH curves for the bladder, and curves 1106a (solid) and 1106b (dashed) show DVH curves for the right femoral head. Additionally, Table 2 can indicate various metrics calculated for both the column generation method and the neural network method.

TABLE 2

| | PTV $D_{98}$ | PTV $D_{99}$ | PTV $D_{max}$ | PTV Homogeneity | Van't Number | $R_{50}$ |
|---|---|---|---|---|---|---|
| Column Generation | 0.984 | 0.970 | 0.898 | 0.065 | 0.915 | 3.598 |
| Neural Network | 0.982 | 0.970 | 0.893 | 0.068 | 0.908 | 3.664 |
| Difference | 0.002 | 0.000 | 0.005 | −0.003 | 0.007 | −0.066 |

Figure 12:
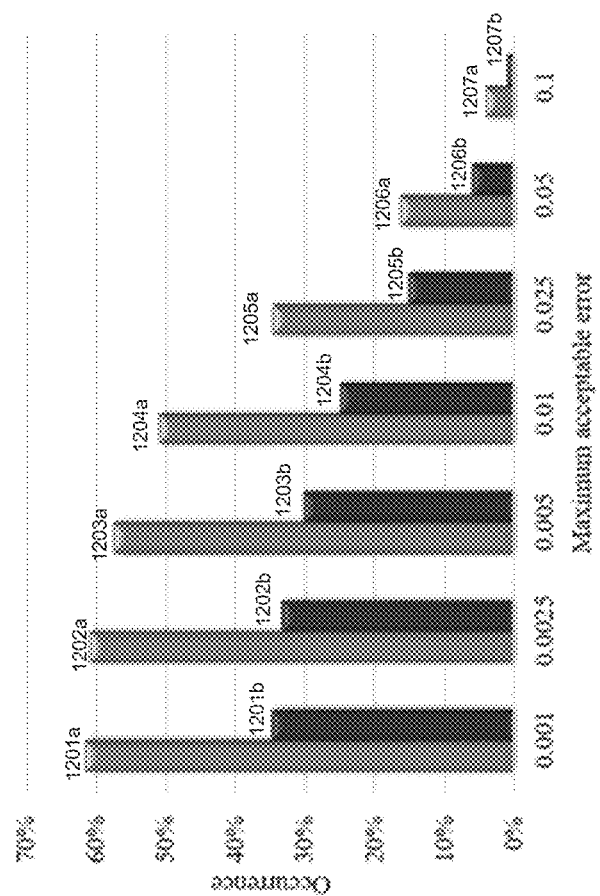
FIG. 12 shows a comparison of fluence map optimization cost functions for a column generation method and a neural network architecture, according to some embodiments of the present disclosure.

FIG. 12 shows a comparison of fluence map optimization cost functions for a column generation method and a neural network architecture, according to some embodiments of the present disclosure. FIG. 12 illustrates percentages of testing scenarios in which column generation found a "better" solution (according to various aforementioned metrics, such as those in Table 2) compared to the neural network approach. Bars 1201a (column generation) and 1201b (neural network) show that, for a maximum acceptable error of 0.001, column generation performed better a little over 60% of the time, while the neural network performed better a little over 35% of the time. Bars 1202-1207 can correspond to larger maximum acceptable error values. Note, as the maximum acceptable error value increases, the column generation and neural network methods become more equal in terms of solution quality. In addition, in some embodiments, predicting a set of five beams with the neural network can take around one and a half seconds, and solving the FMO for each selected beam (assuming five beams, although the network is not limited to predicting five beams) can take approximately twenty-six minutes. The column generation algorithm can take around fifteen hours to complete. Furthermore, the "error" in relation to FIG. 12 refers to how the neural network solutions stray from the column generation algorithm, not how the solution strays in the calculated dose and delivery sense and may not reflect the actual quality of a plan.

Figure 13:
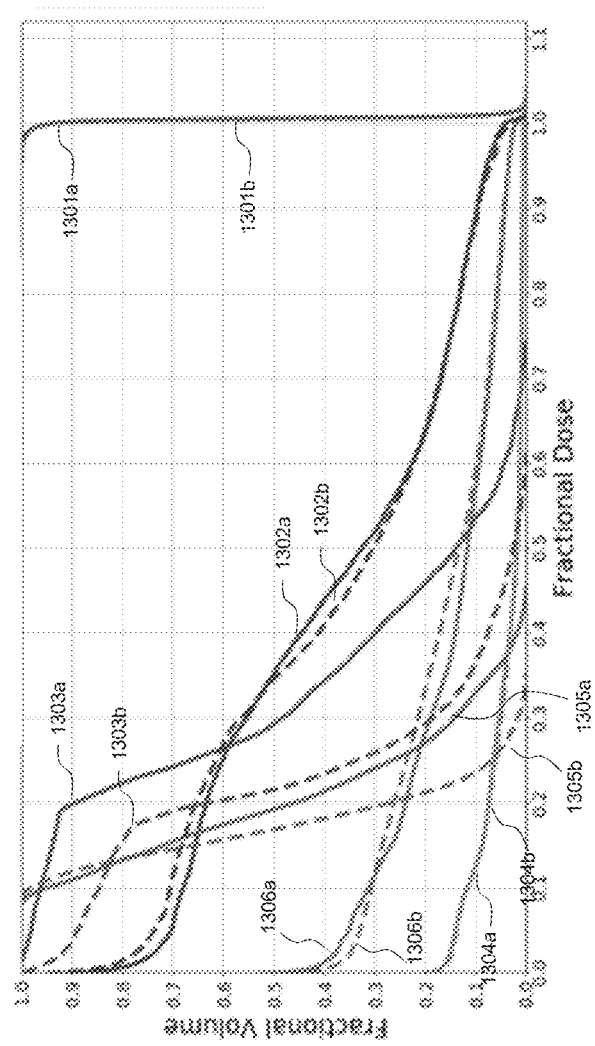
FIG. 13 shows dose volume histogram (DVH) information for a neural network architecture and tree-search algorithm, according to some embodiments of the present disclosure.

FIG. 13 shows dose volume histogram (DVH) information for a neural network architecture and tree-search algorithm, according to some embodiments of the present disclosure. FIG. 13 is similar to FIG. 11, except the DVH histogram in FIG. 13 is for the neural network combined with a tree-search algorithm to select beam orientations. Curve 1301a (solid) and curve 1301b (dashed) show the DVH curse for the PTV and indicates noticeably more radiation is received by the PTV (e.g. prostate cancer) than the normal, non-cancerous organs surrounding the tumor in both methods. Curves 1302a (solid) and 1302b (dashed) show the DVH curves for the rectum, curves 1303a (solid) and 1303b (dashed) show the DVH curves for the right femoral head, curves 1304a (solid) and 1304b (dashed) show the DVH curves for the body, curves 1305a (solid) and 1305b (dashed) show DVH curves for the left femoral head, and curves 1306a (solid) and 1306b (dashed) show DVH curves for the bladder.

FIGS. 14A-14B show self-correction results for a neural network architecture and a column generation algorithm, according to some embodiments of the present disclosure. In some embodiments, self-correction can be used to rectify a poor prediction by the neural network in an early iteration of the network. In some embodiments, plots 1401a-1411a illustrate the iterative process of selecting a set of five beam angles with a column generation algorithm and plots 1401b-1411b illustrate the iterative process of selecting a set of five beam angles using a neural network architecture of the present disclosure that can have self-correction techniques. In some embodiments, the beam selected in plot 1403a is a "better" beam than the beam selected in plot 1403*b*. For example, the cost function resulting from the fitness plots in 1404*a* and 1404*b*, respectively, are 53.021 and 73.815 (note a higher cost function indicates a poorer solution). However, by the time the full beam sets are selected (plots 1411*a* and 1411*b*), the respective cost functions have been reduced to 18.036 and 18.601, suggesting that, even with a poor initial estimate, the neural network architecture is capable of self-correcting and generating a plan comparable to a column generation algorithm.

Figure 15:
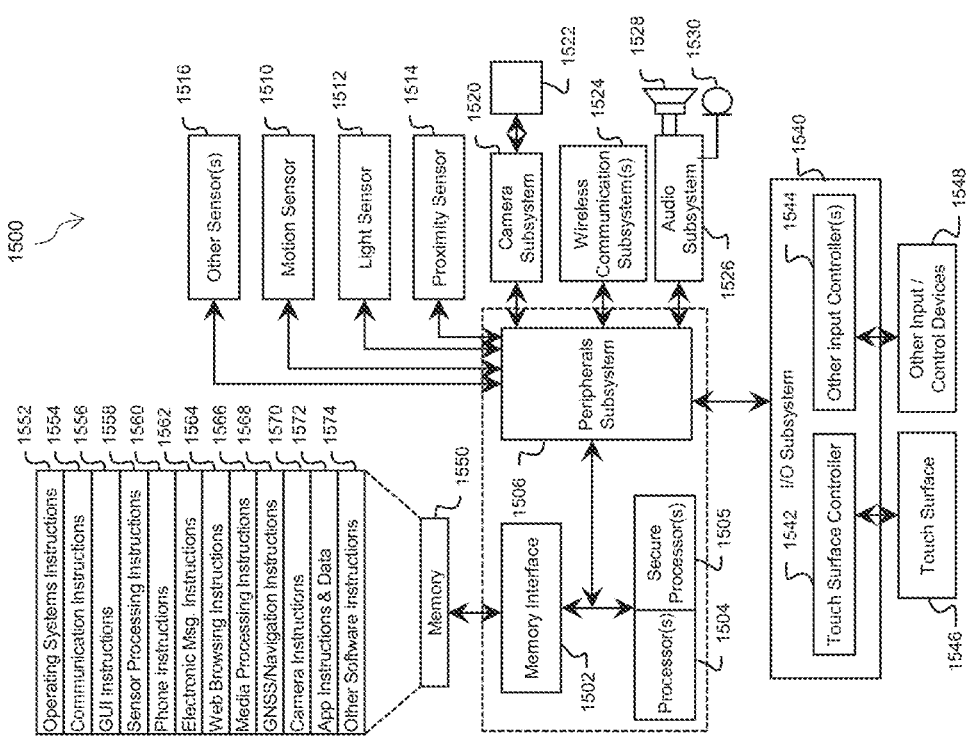
FIG. 15 is an illustrative computing device, according to some embodiments of the present disclosure.

FIG. 15 is an example computing device that may be used within the system of FIG. 1, according to an embodiment of the present disclosure. In some embodiments, device 1500 may be computing device 114. The illustrative user device 1500 may include a memory interface 1502, one or more data processors, image processors, central processing units 1504, and/or secure processing units 1505, and peripherals subsystem 1506. Memory interface 1502, one or more processors 1504 and/or secure processors 1505, and/or peripherals subsystem 1506 may be separate components or may be integrated in one or more integrated circuits. The various components in user device 1500 may be coupled by one or more communication buses or signal lines. Sensors, devices, and subsystems may be coupled to peripherals subsystem 1506 to facilitate multiple functionalities. For example, motion sensor 1510, light sensor 1512, and proximity sensor 1514 may be coupled to peripherals subsystem 1506 to facilitate orientation, lighting, and proximity functions. Other sensors 1516 may also be connected to peripherals subsystem 1506, such as a global navigation satellite system (GNSS) (e.g., GPS receiver), a temperature sensor, a biometric sensor, magnetometer, or other sensing device, to facilitate related functionalities. Camera subsystem 1520 and optical sensor 1522, e.g., a charged coupled device (CCD) or a complementary metal-oxide semiconductor (CMOS) optical sensor, may be utilized to facilitate camera functions, such as recording photographs and video clips. Camera subsystem 1520 and optical sensor 1522 may be used to collect images of a user to be used during authentication of a user, e.g., by performing facial recognition analysis.

Communication functions may be facilitated through one or more wired and/or wireless communication subsystems 1524, which may include radio frequency receivers and transmitters and/or optical (e.g., infrared) receivers and transmitters. For example, the Bluetooth (e.g., Bluetooth low energy (BTLE)) and/or WiFi communications described herein may be handled by wireless communication subsystems 1524. The specific design and implementation of communication subsystems 1524 may depend on the communication network(s) over which the user device 1500 is intended to operate. For example, user device 1500 may include communication subsystems 1524 designed to operate over a GSM network, a GPRS network, an EDGE network, a WiFi or WiMax network, and a Bluetooth™ network. For example, wireless communication subsystems 1524 may include hosting protocols such that device 1500 may be configured as a base station for other wireless devices and/or to provide a WiFi service.

Audio subsystem 1526 may be coupled to speaker 1528 and microphone 1530 to facilitate voice-enabled functions, such as speaker recognition, voice replication, digital recording, and telephony functions. Audio subsystem 1526 may be configured to facilitate processing voice commands, voice-printing, and voice authentication, for example.

I/O subsystem 1540 may include a touch-surface controller 1542 and/or other input controller(s) 1544. Touch-surface controller 1542 may be coupled to a touch surface 1546. Touch-surface 1546 and touch-surface controller 1542 may, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with touch surface 1546.

The other input controller(s) 1544 may be coupled to other input/control devices 1548, such as one or more buttons, rocker switches, thumb-wheel, infrared port, USB port, and/or a pointer device such as a stylus. The one or more buttons (not shown) may include an up/down button for volume control of speaker 1528 and/or microphone 1530.

In some implementations, a pressing of the button for a first duration may disengage a lock of touch-surface 1546; and a pressing of the button for a second duration that is longer than the first duration may turn power to user device 1500 on or off. Pressing the button for a third duration may activate a voice control, or voice command, module that enables the user to speak commands into microphone 1530 to cause the device to execute the spoken command. The user may customize a functionality of one or more of the buttons. Touch-surface 1546 may, for example, also be used to implement virtual or soft buttons and/or a keyboard.

In some implementations, user device 1500 may present recorded audio and/or video files, such as MP3, AAC, and MPEG files. In some implementations, user device 1500 may include the functionality of an MP3 player, such as an iPod™. User device 1500 may, therefore, include a 36-pin connector and/or 8-pin connector that is compatible with the iPod. Other input/output and control devices may also be used.

Memory interface 1502 may be coupled to memory 1550. Memory 1550 may include high-speed random access memory and/or non-volatile memory, such as one or more magnetic disk storage devices, one or more optical storage devices, and/or flash memory (e.g., NAND, NOR). Memory 1550 may store an operating system 1552, such as Darwin, RTXC, LINUX, UNIX, OS X, Windows, or an embedded operating system such as VxWorks.

Operating system 1552 may include instructions for handling basic system services and for performing hardware dependent tasks. In some implementations, operating system 1552 may be a kernel (e.g., UNIX kernel). In some implementations, operating system 1552 may include instructions for performing voice authentication.

Memory 1550 may also store communication instructions 1554 to facilitate communicating with one or more additional devices, one or more computers and/or one or more servers. Memory 1550 may include graphical user interface instructions 1556 to facilitate graphic user interface processing; sensor processing instructions 1558 to facilitate sensor-related processing and functions; phone instructions 1560 to facilitate phone-related processes and functions; electronic messaging instructions 1562 to facilitate electronic messaging-related process and functions; web browsing instructions 1564 to facilitate web browsing-related processes and functions; media processing instructions 1566 to facilitate media processing-related functions and processes; GNSS/Navigation instructions 1568 to facilitate GNSS and navigation-related processes and instructions; and/or camera instructions 1570 to facilitate camera-related processes and functions.

Memory 1550 may store application (or "app") instructions and data 1572, such as instructions for the apps described above in the context of FIGS. 1-14. Memory 1550 may also store other software instructions 1574 for various other software applications in place on device 1500.

Methods described herein may represent processing that occurs within a system for administering radiation therapy treatment plans. The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random-access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, such as EPROM, EEPROM, flash memory device, or magnetic disks. The processor and the memory can be supplemented by, or incorporated in, special purpose logic circuitry.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter. Although the disclosed subject matter has been described and illustrated in the foregoing illustrative embodiments, it is understood that the present disclosure has been made only by way of example, and that numerous changes in the details of implementation of the disclosed subject matter may be made without departing from the spirit and scope of the disclosed subject matter.

The invention claimed is:

1. A method for determining a radiotherapy treatment plan comprising:
   receiving anatomical data for a patient;
   generating, via a neural network analyzing the anatomical data, a plurality of fitness values for a plurality of candidate beam orientations, each fitness value corresponding to a candidate beam orientation of the plurality of candidate beam orientations;
   determining a selected beam orientation based on the plurality of fitness values;
   performing a fluence map optimization (FMO) process on the selected beam orientation; and
   determining a dose distribution for the patient based on the FMO process.

2. The method of claim 1 comprising:
   configuring a multi-leaf collimator (MLC) to administer the dose distribution at the selected beam orientation.

3. The method of claim 1, wherein the anatomical data comprises:
   at least one image of a tumor within the patient, wherein each of the at least one image comprises contours defining a plurality of organs at risk (OARs); and
   a plurality of structure weights associated with the plurality of OARs, wherein each structure weight corresponds to a respective OAR of the plurality of OARs.

4. The method of claim 1, wherein determining the selected beam orientation comprises using an argmax function to identify a beam orientation associated with a maximum or a minimum fitness value of the plurality of fitness values.

5. The method of claim 1, wherein determining the selected beam orientation comprises using a tree-search algorithm to identify a solution from a decision space of the neural network.

6. The method of claim 5, wherein using a tree-search algorithm to identify the solution from the decision space of the neural network comprises iteratively selecting a branch based on a probability distribution of the neural network and updating the probability distribution after each selection.

7. The method of claim 1, wherein each fitness value of the plurality of fitness values is a prediction of a value based on dual feasibility optimality conditions.

8. The method of claim 1, wherein the neural network comprises a convolutional up-sampling stage.

9. A method for determining a radiotherapy treatment plan comprising:
- receiving anatomical data for a patient;
- receiving beam orientation data, wherein the beam orientation data comprises information on pre-selected beam orientations;
- generating, via a neural network analyzing the anatomical data and the beam orientation data, a first plurality of fitness values for a plurality of candidate beam orientations, each fitness value corresponding to a candidate beam orientation of the plurality of candidate beam orientations;
- determining a first selected beam orientation based on the first plurality of fitness values;
- generating updated beam orientation data that comprises information associated with the first selected beam orientation;
- generating, via the neural network analyzing the anatomical data and the updated beam orientation data, a second plurality of fitness values for the plurality of candidate beam orientations, each fitness value corresponding to a candidate beam orientation of the plurality of candidate beam orientations;
- determining a second selected beam orientation based on the second plurality of fitness values;
- performing a fluence map optimization (FMO) process on the first and second selected beam orientations; and
- determining a dose distribution for the patient based on the FMO process.

10. The method of claim 9 comprising:
- configuring a multi-leaf collimator (MLC) to administer the dose distribution at the first and second selected beam orientations.

11. The method of claim 9, wherein the anatomical data comprises:
- at least one image of a tumor within the patient, wherein each of the at least one image comprises contours defining a plurality of organs at risk (OARs); and
- a plurality of structure weights associated with the plurality of OARs, wherein each structural weight corresponds to a respective OAR.

12. The method of claim 9, wherein determining the first selected beam orientation comprises using an argmax function to identify a beam orientation associated with a maximum or a minimum fitness value of the first plurality of fitness values; and
- wherein determining the second selected beam orientation comprises using an argmax function to identify a beam orientation associated with a maximum or a minimum fitness value of the second plurality of fitness values.

13. The method of claim 9, wherein at least one of determining the first selected beam orientation or the second selected beam orientation comprises using a tree-search algorithm to identify a solution from a decision space of the neural network.

14. The method of claim 13, wherein using a tree-search algorithm to identify the solution from the decision space of the neural network comprises iteratively selecting a branch based on a probability distribution of the neural network and updating the probability distribution after each selection.

15. The method of claim 9, wherein each fitness value of the first and second pluralities of fitness values is a prediction of a value based on dual feasibility optimality conditions.

16. The method of claim 9, wherein generating, via the neural network analyzing the anatomical data and the beam orientation data, the first plurality of fitness values for the plurality of candidate beam orientations comprises:
- generating a complement of the beam orientation data; and
- generating the first plurality of fitness values for the plurality of candidate beam orientations based on the anatomical data, the beam orientation data, and the complement of the beam orientation data.

17. The method of claim 9, wherein the neural network comprises a convolutional up-sampling stage.

* * * * *